(12) United States Patent
Martin et al.

(10) Patent No.: US 9,260,692 B2
(45) Date of Patent: *Feb. 16, 2016

(54) USE OF MODIFIED CELLS FOR THE TREATMENT OF MULTIPLE SCLEROSIS

(71) Applicant: UNIVERSITAT ZURICH, Zurich (CH)

(72) Inventors: Roland Martin, Zurich (CH); Andreas Lutterotti, Mils (AT)

(73) Assignee: UNIVERSITAT ZURICH, Zurich (CH)

( * ) Notice: Subject to any disclaimer, the term of this patent is extended or adjusted under 35 U.S.C. 154(b) by 156 days.

This patent is subject to a terminal disclaimer.

(21) Appl. No.: 14/218,378

(22) Filed: Mar. 18, 2014

(65) Prior Publication Data

US 2014/0212445 A1    Jul. 31, 2014

Related U.S. Application Data

(63) Continuation-in-part of application No. 12/740,502, filed as application No. PCT/EP2008/009204 on Oct. 31, 2007, now Pat. No. 8,673,293.

(30) Foreign Application Priority Data

Oct. 31, 2007    (EP) .................................... 07075952

(51) Int. Cl.
| | |
|---|---|
| *C12N 5/00* | (2006.01) |
| *A61K 39/00* | (2006.01) |
| *C12N 5/078* | (2010.01) |
| *A61K 45/06* | (2006.01) |
| *A61K 35/17* | (2015.01) |
| *A61K 35/18* | (2015.01) |

(52) U.S. Cl.
CPC .............. *C12N 5/0006* (2013.01); *A61K 35/17* (2013.01); *A61K 35/18* (2013.01); *A61K 39/0008* (2013.01); *A61K 45/06* (2013.01); *C12N 5/0634* (2013.01); *C12N 5/0641* (2013.01)

(58) Field of Classification Search
None
See application file for complete search history.

(56) References Cited

U.S. PATENT DOCUMENTS

| 8,673,293 B2 | 3/2014 | Martin et al. |
| 2011/0033426 A1 | 2/2011 | Martin et al. |

FOREIGN PATENT DOCUMENTS

WO    2009056332 A1    5/2009

OTHER PUBLICATIONS

KK Tsilidis et al. "Evaluation of Excess Significance Bias in Animal Studies of Neurological Diseases." PLoS Biol. Jul. 2013;11(7):e1001609; Epub Jul. 16, 2013.
J Mestas et al. "Of mice and not men: differences between mouse and human immunology." J Immunol. Mar. 1, 2004;172(5):2731-8.
JM Chase "The shadow of bias." PLoS Biol. Jul. 2013;11(7):e1001608; Epub Jul. 16, 2013.
A Lutterotti et al. "Antigen-specific tolerance by autologous myelin peptide-coupled cells: a phase 1 trial in multiple sclerosis." Sci Trans! Med. 5(188); Jun. 5, 2013.
Bielekova B et al. "Expansion and Functional Relevance of High-Avidity Myelin-Specific CD4 <+> T Cells in Multiple Sclerosis." (Journal of Immunology), Mar. 15, 2004, 3893-3904, 172: 6.
Kohm, Adam P et al. "Targeting the TCR: T-cell receptor and peptide-specific tolerance-based strategies for restoring self-tolerance in CNS autoimmune disease." (International Reviews of Immunology), Sep. 2005, 361-392, 24: 5.
Martin R et al. "Future therapeutic options for multiple sclerosis." (Aktuelle Neurologie), May 2008, 169-176, 35: 4.
Miller, Stephen D et al. "Antigen-specific tolerance strategies for the prevention of treatment of autoimmune disease." (Nature Reviews Immunology), Sep. 2007, 665-677, 7: 9.
Ponomarenko Natalia A et al. "Autoantibodies to myelin basic protein catalyze site-specific degradation of their antigen." (Proceedings of the National Academy of Science of the United States of America), Jan. 2006, 281-286, 103: 2.
Smith et al. "Multi-peptide coupled-cell tolerance ameliorates ongoing relapsing EAE associated with multiple pathogenic autoreactivities." (Journal of Autoimmunity), Feb. 6, 2007, 218-231, 27: 4.
Sorbera L. A. "MBP-8298. Agent for Multiple Sclerosis." (Drugs of the Future), Oct. 2006, 864-866, 31: 10.
Sospedra, Mireia et al. "Immunology of multiple sclerosis." (Annual Review of Immunology), 2005, 683-747, 23.
Turley, Danielle M et al. "Peripheral tolerance induction using ethylenecarbodiimide-fixed APCs uses both direct and indirect mechanisms of antigen presentation for prevention of experimental autoimmune encephalomyelitis." (Journal of Autoimmunology), Feb. 2007, 2212-2220, 178: 4.
Vandenbark, Arthur A et al. "Differential susceptibility of human Th1versus Th2 cells to induction of anergy and apoptosis by EDCI/antigen-coupled antigen-presenting cells." (International Immunology), Jan. 2000, 57-66, 12: 1.
Warren K G et al. "Intravenous synthetic peptide MBP8298 delayed disease progression in an HLA Class II-defined cohort of patients with progressive multiple sclerosis: results of a 24-month double-blind placebo-controlled clinical trial and 5 years of follow-up treatment." (European Journal of Neurology), Aug. 2006, 887-895, 13:8.
R. Martin et al "Citrulline-containing myelin basic protein is recognized by T-cell lines derived from jultiple sclerosis patients and healthy individuals" Neurology [1994], vol. 44, pp. 123-129.
H.S. Dua et al. "Inhibition of Experimental Autoimmune Uveitis by Retinal Photoreceptor Antigens Coupled to Spleen Cells" Cellular Immunology, [1992], vol. 139, pp. 292-305.
L. J. Drager et al. "DALI-the first human whole-blood low-density lipoprotein and lipoprotein (a) apheresis system in clinical use: procedure and clinical results" European Journal of Clinical Investigation, [1998], vol. 28, pp. 994-1002.
A. B. Moshnikova et al. "Cytotoxic activity of 1-ethyl-3-(3-dimethylaminopropyl)-carbodiimide is underlain by DNA interchain cross-linking" Cellular and Molecular Life Sciences, [2006], vol. 63, pp. 229-234.
Rachel Schneerson et al. "Preparation, Characterization, and Immunogenicity of Haemophilus Influenzae Type b Polysaccharide-Protein Conjugates" Journal of Experimental Medicine, [1980], vol. 152, pp. 361-376.
K. G. Warren et al. "Tolerance induction to myelin basic protein by intravenous synthetic peptides containing epitope P85 VVHFFKNIVTP96 in chronic progressive multiple sclerosis" Journal of Neurological Sciences, [1997], vol. 152, pp. 31-38.

(Continued)

*Primary Examiner* — Rosanne Kosson
*Assistant Examiner* — Aaron J Kosar
(74) *Attorney, Agent, or Firm* — JMB Davis Ben-David

(57) ABSTRACT

The present invention describes blood cells chemically coupled with immunodominant myelin peptides and their use in the treatment of Multiple Sclerosis.

19 Claims, 9 Drawing Sheets
(7 of 9 Drawing Sheet(s) Filed in Color)

(56) References Cited

OTHER PUBLICATIONS

Mary K. Kennedy et al. "Specific Immune Regulation of Chronic-Relapsing Experimental Allergic Encephalomyelitis in Mice" Journal of Immunology, [1988], vol. 141, No. 9, pp. 2986-2993.

Stephen D. Miller et al. "The induction of cell-mediated immunity and tolerance with protein antigens couples to syngeneic lymphoid cells" Journal of Experimental Medicine, [1979], vol. 149, pp. 758-773.

Lit-Jen Tan et al. "Successful Treatment of Paralytic Relapses in Adoptive Experimental Autoimmune Encephalomyelitis Via Neuroantigen-Specific Tolerance" Journal of Immunology, [1991], vol. 147, No. 6, pp. 1797-1802.

Meir Wilchek et al. "A Highly Sensitive Colorimetric Method of the Determination of Carbodiimides" Analytical Biochemistry, [1981], vol. 114, pp. 419-421.

Helen Braley-Mullen et al. "Suppression of Experimental Autoimmune Thyroiditis in the Guinea Pig by Pretreatment with Thyroglobulin in Incomplete Freund's Adjuvant" Cellular Immunology, [1978], vol. 39, pp. 289-296.

Marc K. Jenkins et al. Antigen Presentation by Chemically Modified Splenocytes Induces Antigen-Specific T Cell Unresponsiveness In Vitro and In Vivo Journal of Experimental Medicine, [1987], vol. 165, pp. 302-319.

Bibiana Bielekova et al. "Encephalitogenic potential of the myelin basic protein peptide (amino acids 83-99) in multiple sclerosis: Results of a phase II clinical trial with an altered peptide ligand" Nature Medicine [2000], vol. 6, No. 10, pp. 1167-1175.

Mary K. Kennedy et al. "Regulation of the Effector Stages of Experimental Autoimmune Encephalomyelitis Via Neuroantigen-Specific Tolerance Induction" Journal of Immunology, [1990], vol. 145, No. 1, pp. 117-126.

Mary K. Kennedy et al. "Inhibition of Murine Relapsing Experimental Autoimmune Encephalomyelitis by Immune Tolerance to Proteolipid Protein and its Encephalitogenic Peptides" Journal of Immunology, [1990], vol. 144, No. 3, pp. 909-915.

Cassandra E. Smith et al. "Differential induction of IgE-mediated anaphylaxis after soluble vs. cell-bound tolerogenic peptide therapy of autoimmune encephalomyelitis" PNAS, [2005], vol. 102, No. 27, pp. 9595-9600.

Lit-Jen Tan et al. "Regulation of the effector Stages of Experimental Autoimmune Encephalomyelitis Via Neuroantigen-Specific Tolerance Induction" Journal of Immunology, [1992], vol. 148, No. 9, pp. 2748-2755.

Carol L. Vanderlugt et al. "Pathologic Role and Temporal Appearance of Newly Emerging Autoepitopes in Relapsing Experimental Autoimmune Encephalomyelitis" Journal of Immunology, [2000], vol. 164, pp. 670-678.

Shahik K. Gregorian et al. "Induction of Peripheral Tolerance with Peptide-Specific Anergy in Experimental Autoimmune Neuritis" Cellular Immunology, [1993], vol. 150, pp. 298-310.

E.C. Beuvery et al. "Analytical, Toxicological and Immunological Consequences of the use of N-Ethyl-N'-(3-Dimethylaminopropyl) Carbodiimide as coupleing reagent for the preparation of Meningococcal Group C Polysaccharide-Tetanus Toxoid Conjugate as vaccine for human use" Develop. Biol. Standard., [1986], vol. 63, pp. 117-128.

John Kamholz et al. "Identification of three forms of human myelin basic protein by cDNA cloning" Neurobiology, [1986], vol. 83, pp. 4962-4966.

Louise Pope et al. "Antigen-specific inhibition of the adoptive transfer of experimental autoimmune encephalomyelitis in Lewis rats" Journal of Neuroimmunology, [1992], vol. 37, pp. 177-190.

Laura R. Tranquill et al. "Enhanced T Cell Responsiveness to Citrulline-Containing Myelin Basic Protein in Multiple Sclerosis Patients" Multiple Sclerosis, [2000], vol. 6, pp. 220-225.

Kevin J. Kennedy et al. "Induction of Antigen-Specific Tolerance for the Treatment of Ongoing, Relapsing Autoimmune Encephalomyelitis" Journal of Immunology, [1997], vol. 159, pp. 1036-1044.

A. A. Vandenbark et al. "Prevention and Treatment of Relapsing Autoimmune Encephalomyelitis With Myelin Peptide-Coupled Splenocytes" Journal of Neuroscience Research, [1996], vol. 45, pp. 430-438.

Mario A. Moscarello et al. "The Role of Citrullinated Proteins Suggests a Novel Mechanism in the Pathogenesis of Multiple Sclerosis" Neurochem Res, [2007], vol. 32, pp. 251-256.

Streptavidin Cy3

| | biotinPLP130-154 | EDC |
|---|---|---|
| 1 open histogram | - | - |
| 2 open histogram | - | + |
| 3 open histogram | + | - |
| 4 filled histogram | + | + |

Streptavidin Cy3

Streptavidin APC

Open histogram    PBMC after lysis, before coupling reaction

Filled histogram   Product (PBMC after coupling reaction)

USE OF MODIFIED CELLS FOR THE TREATMENT OF MULTIPLE SCLEROSIS

This application is a continuation-in-part of U.S. Ser. No. 12/740,502, filed Oct. 13, 2010, now issued as U.S. Pat. No. 8,673,293, which is a U.S. National Stage under §371 of PCT/EP2008/009204, filed Oct. 31, 2008, which applications claim priority to EP07075952.7, filed Oct. 31, 2007.

SEQUENCE LISTING

The instant application contains a Sequence Listing which has been submitted electronically in ASCII format and is hereby incorporated by reference in its entirety. Said ASCII copy, created on Apr. 3, 2014, is named 0079-P01 Squ Lstg.txt and is 12,471 bytes in size.

Multiple sclerosis (MS) is a devastating autoimmune inflammatory disease of the brain and spinal cord mainly affecting young adults.

Multiple sclerosis (MS) is the most frequent debilitating neurological disease of young adults in Europe (prevalFence 60-200/100,000, incidence 2-4/100,000), with half of patients needing a walking aid 10-15 years from onset of the disease. MS ranks second only to trauma in the age group of young adults with respect to socioeconomic costs. The symptoms of MS vary, depending on the location of lesions within the CNS, including focal weakness, sensory deficits, double vision, loss of vision, imbalance, fatigue, urinary and bowel dysfunction, sexual impairment and cognitive decline. In most patients the disease starts with a relapsing-remitting disease course (RR-MS), which is followed by a secondary progressive deterioration usually beginning about ten years after disease onset (SP-MS). The etiology is unknown, but it is well accepted that the damage in the central nervous system (CNS) results from an autoimmune attack against (auto) antigens within the myelin sheath. Currently approved therapies for MS involve various antigen-nonspecific immunomodulating or immunosuppressive strategies, which are only partially effective in that they prevent 30%-50% of relapses. Preventing progression of disability has not been consistently demonstrated for these therapies, yet. However, most current therapeutics need to be injected for long periods of time and are associated with considerable side effects. Particularly in a chronic disease as MS, therapy should aim to specifically delete or functionally inhibit pathogenic autoreactive cells without altering the "normal" immune system. This is of importance because global immunomodulation and/or immunesuppression come at the cost of inhibiting beneficial regulatory cells and immune cells that might serve protective functions. Thus the ideal treatment would be early intervention using an antigen-specific tolerance protocol that selectively targets both activated and naïve autoreactive T cells specific for multiple potential encephalitogenic epitopes that perpetuate the disease.

The mechanisms responsible for tissue damage in MS involve the activation of self-reactive T lymphocytes which attack proteins in the myelin sheath. Current therapies for MS inhibit the autoimmune response in a nonspecific manner, are only moderately effective and can have significant side effects. Based on success in pre-clinical experiments in animal models of MS, embodiments of the present application provide a new therapeutic strategy, which will specifically target only the autoreactive CD4+ T lymphocytes. Tolerance will be induced by a single administration of blood cells, in particular red blood cells (erythrocytes) or peripheral blood mononuclear cells (PBMCs) chemically coupled with a mixture of synthetic myelin antigens to which T cell responses are demonstrable in early MS patients. The therapy is exquisitely antigen-specific and renders autoreactive T cells non-functional or anergic.

The induction of tolerance to target autoantigens is a highly important therapeutic goal in autoimmune diseases. It offers the opportunity to attenuate specifically the pathogenic autoimmune response in an effective way with few side effects. To achieve this goal, embodiments of the present application provide a very promising tolerization strategy that employs autologous peptide-pulsed, fixed, antigen presenting cells as tolerogen. This therapy has proven excellent efficacy in animal models of MS and different T cell-mediated autoimmune diseases.

The therapy is based on systemic administration of blood cells chemically coupled with a cocktail of peptides containing at least five of eight immunodominant myelin peptides ($MBP_{13-32}$, $MBP_{83-99}$, $MBP_{111-129}$, $MBP_{146-170}$, $PLP_{139-154}$, $MOG_{1-20}$, $MOG_{35-55}$ and $MBP_{82-98}$), to which T cell responses are demonstrable in early RR-MS patients. Preferred is the use of six, seven, or eight of the named immunodominant myelin peptides ($MBP_{13-32}$, $MBP_{83-99}$, $MBP_{111-129}$, $MBP_{146-170}$, $PLP_{139-154}$, $MOG_{1-20}$, $MOG_{35-55}$ and $MBP_{82-98}$).

An alternative therapy is based on systemic administration of blood cells chemically coupled with a cocktail of peptides containing at least five of twenty immunodominant myelin peptides ($MBP_{13-32}$, $MBP_{83-99}$, $MBP_{111-129}$, $MBP_{82-98}$, $MBP_{82-99}$, $MBP_{82-106}$, $MBP_{87-106}$, $MBP_{131-155}$, $MBP_{146-170}$, $PLP_{41-58}$, $PLP_{89-106}$, $PLP_{95-116}$, $PLP_{139-154}$, $PLP_{178-197}$, $PLP_{190-209}$, $MOG_{1-20}$, $MOG_{11-30}$, $MOG_{21-40}$, $MOG_{35-55}$, $MOG_{64-86}$), to which T cell responses are demonstrable in early RR-MS patients. Preferred is the use of six, seven, eight or even more (up to 14, see table 5) of the named immunodominant myelin peptides ($MBP_{13-32}$, MBP 83-99, MBP 111-129, $MBP_{82-98}$, $MBP_{82-99}$, $MBP_{82-106}$, $MBP_{87-106}$, $MBP_{131-155}$, $MBP_{146-170}$, $PLP_{41-58}$, $PLP_{89-106}$, $PLP_{95-116}$, $PLP_{139-154}$, $PLP_{178-197}$, $PLP_{190-209}$, $MOG_{1-20}$, $MOG_{11-30}$, $MOG_{21-40}$, $MOG_{35-55}$, $MOG_{64-86}$).

The blood cells may be autologous (relative to the treated subject) in case of peripheral blood mononuclear cells (PBMCs) and in case of red blood cells (erythrocytes) or the blood cells or may be allogeneic (relative to the treated subject) in case of red blood cells (erythrocytes).

Preferred blood cells are red blood cells (erythrocytes) and peripheral blood mononuclear cells (PBMCs). The preferred route for systemic administration is i.v. administration.

A preferred aspect of the invention is therefore a therapy based on systemic administration of autologous peripheral blood mononuclear cells chemically coupled with a cocktail containing at least five of eight immunodominant myelin peptides ($MBP_{13-32}$, $MBP_{83-99}$, $MBP_{111-129}$, $MBP_{146-170}$, $PLP_{139-154}$, $MOG_{1-20}$, $MOG_{35-55}$ and $MBP_{82-98}$), to which T cell responses are demonstrable in early RR-MS patients. Preferred is the use of six, seven or eight of the named immunodominant myelin peptides ($MBP_{13-32}$, $MBP_{83-99}$, $MBP_{111-129}$, $MBP_{146-170}$, $PLP_{139-154}$, $MOG_{1-20}$, $MOG_{35-55}$ and $MBP_{82-98}$).

A further preferred aspect of the invention is therefore a therapy based on systemic administration of red blood cells or erythrocytes (which may be autologous or allogeneic) chemically coupled with a cocktail containing at least five of twenty immunodominant myelin peptides ($MBP_{13-32}$, $MBP_{83-99}$, $MBP_{111-129}$, $MBP_{82-98}$, $MBP_{82-99}$, $MBP_{82-106}$, $MBP_{87-106}$, $MBP_{131-155}$, $MBP_{146-170}$, $PLP_{41-58}$, $PLP_{89-106}$, $PLP_{95-116}$, $PLP_{139-154}$, $PLP_{178-197}$, $PLP_{190-209}$, $MOG_{1-20}$, $MOG_{11-30}$, $MOG_{21-40}$, $MOG_{35-55}$, $MOG_{64-86}$), to which T cell responses are demonstrable in early RR-MS patients. Preferred is the use of six, seven, eight or even more (up to 14) of the named immunodominant myelin peptides ($MBP_{13-32}$, $MBP_{83-99}$, $MBP_{111-129}$, $MBP_{82-98}$, $MBP_{82-99}$, $MBP_{82-106}$, $MBP_{87-106}$, $MBP_{131-155}$, $MBP_{146-170}$, $PLP_{41-58}$, $PLP_{89-106}$, $PLP_{95-116}$, $PLP_{139-154}$, $PLP_{178-197}$, $PLP_{190-209}$, $MOG_{1-20}$, $MOG_{11-30}$, $MOG_{21-40}$, $MOG_{35-55}$, $MOG_{64-86}$).

Even more preferred is the use of one of a cocktail of peptides, wherein the cocktail is selected from:
a) $MBP_{13-32}$, $MBP_{83-99}$, $MBP_{111-129}$, $MBP_{146-170}$, $PLP_{139-154}$, $MOG_{1-20}$ and $MOG_{35-55}$
b) $MBP_{13-32}$, $MBP_{82-98}$, $MBP_{111-129}$, $MBP_{146-170}$, $PLP_{139-154}$, $MOG_{1-20}$ and $MOG_{35-55}$
c) $MBP_{13-32}$, $MBP_{83-99}$, $MBP_{111-129}$, $MBP_{146-170}$, $PLP_{139-154}$, $MOG_{1-20}$, $MOG_{35-55}$ and $MBP_{82-98}$
d) $MBP_{13-32}$, $MBP_{111-129}$, $MBP_{146-170}$, $PLP_{139-154}$, $MOG_{1-20}$ and $MOG_{35-55}$.

Further preferred cocktails for use in a method disclosed in this application are cocktails e-oo according to following tables 5.1-5.3. The individual cocktails are disclosed in the columns of said tables. An "X" indicates that the peptide named in the most left column of the table is present in the cocktail. The numbering of the cocktails is provided in the top line of the tables.

TABLE 5.1

Preferred cocktails of peptides e-p for use in the methods disclosed herein:

| | e | f | g | h | i | j | k | l | m | n | o | p |
|---|---|---|---|---|---|---|---|---|---|---|---|---|
| $MBP_{13-32}$ | X | | | | X | X | X | X | | X | X | |
| $MBP_{83-99}$ | | X | | | X | | | | | | | |
| $MBP_{82-98}$ | | | X | | | | | | | | | |
| $MBP_{82-99}$ | | | | | | | | | | | | |
| $MBP_{82-106}$ | X | X | X | X | | X | X | X | X | X | X | |
| $MBP_{87-106}$ | | | | | | | | | | | | |
| $MBP_{131-155}$ | | X | X | | | X | X | | | X | X | |
| $MBP_{111-129}$ | X | | | | X | X | X | X | | | X | X |
| $MBP_{146-170}$ | X | X | | | X | X | X | X | X | X | X | |
| $PLP_{41-58}$ | | | | X | | | X | | | | | X |
| $PLP_{89-106}$ | | X | | | | | X | X | | | | X |
| $PLP_{95-116}$ | | | X | | | | X | | | | | X |
| $PLP_{139-154}$ | X | | | | X | X | X | X | X | X | X | X |
| $PLP_{178-197}$ | | | | | | X | X | | X | X | | X |
| $PLP_{190-209}$ | | | X | | | | X | X | | X | | X |
| $MOG_{1-20}$ | X | | | | X | X | X | X | | | | |
| $MOG_{11-30}$ | | | | | | | | X | | | | |
| $MOG_{21-40}$ | | | | | | | | X | | | | |
| $MOG_{35-55}$ | X | | | | X | X | X | X | X | X | X | X |
| $MOG_{64-86}$ | | | | | | | X | | | | | |

TABLE 5.2

Preferred cocktails of peptides q-bb for use in the methods disclosed herein:

| | q | r | s | t | u | v | w | x | y | z | aa | bb |
|---|---|---|---|---|---|---|---|---|---|---|---|---|
| $MBP_{13-32}$ | | X | X | X | X | X | X | X | X | X | X | X |
| $MBP_{83-99}$ | | | | | | | | | | | | X |
| $MBP_{82-98}$ | | | | | | | | | | | | |
| $MBP_{82-99}$ | | | | | | | | | | | X | X |
| $MBP_{82-106}$ | X | X | X | X | X | X | X | X | X | X | | |
| $MBP_{87-106}$ | | | | | | | | | | | | X |
| $MBP_{131-155}$ | | X | X | X | X | X | X | | | | | |
| $MBP_{111-129}$ | | X | X | X | X | X | X | X | | | X | X |
| $MBP_{146-170}$ | | X | X | X | X | X | X | X | X | X | X | X |
| $PLP_{41-58}$ | | X | | | | | | | | | | |
| $PLP_{89-106}$ | | | X | | | | | X | X | | X | X |
| $PLP_{95-116}$ | | | | X | | | | | | | | |
| $PLP_{139-154}$ | X | | | | | | | X | X | X | X | X |
| $PLP_{178-197}$ | | | | | X | | | X | X | X | | X |
| $PLP_{190-209}$ | | | | | | X | | X | X | X | X | X |
| $MOG_{1-20}$ | X | | | | | | | X | X | X | X | X |
| $MOG_{11-30}$ | X | | | | | | | | | X | | |
| $MOG_{21-40}$ | X | | | | | | | | | X | | |
| $MOG_{35-55}$ | X | X | X | X | X | X | X | X | X | X | X | X |
| $MOG_{64-86}$ | X | | | | | | | | | X | | |

TABLE 5.3

Preferred cocktails of peptides cc-oo for use in the methods disclosed herein:

| | cc | dd | ee | ff | gg | hh | ii | jj | kk | ll | mm | nn | oo |
|---|---|---|---|---|---|---|---|---|---|---|---|---|---|
| $MBP_{13-32}$ | X | | X | | X | | X | | | X | X | X | |
| $MBP_{83-99}$ | | | | | | | | | | | | | X |
| $MBP_{82-98}$ | | | | | | | | | | | | | |
| $MBP_{82-99}$ | | | | | | | | | | | | | |
| $MBP_{82-106}$ | | | | | | | | | | | X | X | |
| $MBP_{87-106}$ | X | X | X | X | X | X | X | X | X | | | | |
| $MBP_{131-155}$ | | | | | | | | | | X | | | |
| $MBP_{111-129}$ | X | X | | | | X | | | X | | X | | X |
| $MBP_{146-170}$ | X | X | X | X | | | X | | X | | X | | X |
| $PLP_{41-58}$ | X | X | X | | | | | | | X | | | |
| $PLP_{89-106}$ | | X | X | | | | X | | | | X | | |
| $PLP_{95-116}$ | | X | | | | | | | | | X | | |
| $PLP_{139-154}$ | X | X | X | X | X | X | X | X | | | X | | X |
| $PLP_{178-197}$ | X | X | | | | | | | X | | X | | |
| $PLP_{190-209}$ | X | X | X | | X | | | X | X | | X | | |
| $MOG_{1-20}$ | X | X | | X | X | X | X | X | | | X | | X |
| $MOG_{11-30}$ | | | | X | | | | | | | X | | |
| $MOG_{21-40}$ | | | | X | | | | | | | X | | |
| $MOG_{35-55}$ | X | X | X | X | X | X | X | X | | | X | X | X |
| $MOG_{64-86}$ | | | | X | | | | | | | X | X | |

In each of the cocktails described herein a MBP peptide may also be replaced with the full length MBP protein. Most preferred of the known MBP proteins is the 18.5 kD isoform (SEQ ID NO: 22). Furthermore any of the MBP peptides may be citrullinated. Moreover, any of the MBP peptides may be replaced with a citrullinated peptide according to SEQ ID NOs: 24-26.

In each of the cocktails described herein a PLP peptide may also be replaced with the full length PLP protein (SEQ ID NO: 21).

In each of the cocktails described herein a MOG peptide may also be replaced with the full length MOG protein (SEQ ID NO: 23).

Most preferred in this aspect of the invention is the use of the cocktail consisting of the following seven peptides $MBP_{13-32}$, $MBP_{83-99}$, $MBP_{111-129}$, $MBP_{146-170}$, $PLP_{139-154}$, $MOG_{1-20}$ and $MOG_{35-55}$.

The preferred route for systemic administration is i.v. administration.

Another preferred aspect of the invention is therefore a therapy based on systemic administration of allogeneic peripheral blood mononuclear cells or red blood cells (erythrocytes) chemically coupled with a cocktail containing at least five of eight immunodominant myelin peptides ($MBP_{13-32}$, $MBP_{83-99}$, $MBP_{111-129}$, $MBP_{146-170}$, $PLP_{139-154}$, $MOG_{1-20}$, $MOG_{35-55}$ and $MBP_{82-98}$), to which T cell responses are demonstrable in early RR-MS patients. Preferred is the use of six, seven or eight of the named immunodominant myelin peptides ($MBP_{13-32}$, $MBP_{83-99}$, $MBP_{111-129}$, $MBP_{146-170}$, $PLP_{139-154}$, $MOG_{1-20}$, $MOG_{35-55}$ and $MBP_{82-98}$).

Most preferred in this aspect is the use of the cocktail consisting of the following seven peptides $MBP_{13-32}$, $MBP_{83-99}$, $MBP_{111-129}$, $MBP_{146-170}$, $PLP_{139-154}$, $MOG_{1-20}$ and $MOG_{35-55}$.

A still further preferred aspect of the invention is therefore a therapy based on systemic administration of allogeneic peripheral blood mononuclear cells or red blood cells (erythrocytes) chemically coupled with a cocktail containing at least five of twenty immunodominant myelin peptides ($MBP_{13-32}$, $MBP_{83-99}$, $MBP_{111-129}$, $MBP_{82-98}$, $MBP_{82-99}$, $MBP_{82-106}$, $MBP_{87-106}$, $MBP_{131-155}$, $MBP_{146-170}$, $PLP_{41-58}$, $PLP_{89-106}$, $PLP_{95-116}$, $PLP_{139-154}$, $PLP_{178-197}$, $PLP_{190-209}$, $MOG_{1-20}$, $MOG_{11-30}$, $MOG_{21-40}$, $MOG_{35-55}$, $MOG_{64-86}$), to which T cell responses are demonstrable in early RR-MS patients. Preferred is the use of six, seven, eight or even more (up to 14) of the named immunodominant myelin peptides ($MBP_{13-32}$, $MBP_{83-99}$, $MBP_{111-129}$, $MBP_{82-98}$, $MBP_{82-99}$, $MBP_{82-106}$, $MBP_{87-106}$, $MBP_{131-155}$, $MBP_{146-170}$, $PLP_{41-58}$, $PLP_{89-106}$, $PLP_{95-116}$, $PLP_{139-154}$, $PLP_{178-197}$, $PLP_{190-209}$, $MOG_{1-20}$, $MOG_{11-30}$, $MOG_{21-40}$, $MOG_{35-55}$, $MOG_{64-86}$).

Most preferred in this aspect is the use of the cocktail consisting of the following seven peptides $MBP_{13-32}$, $MBP_{83-99}$, $MBP_{111-129}$, $MBP_{146-170}$, $PLP_{139-154}$, $MOG_{1-20}$ and $MOG_{35-55}$.

The preferred route for systemic administration is i.v. administration.

Extensive immunological studies, including human in-vitro studies and animal in-vitro and in vivo studies do document the safety, efficacy and in vivo mechanisms of action of the regimens described above.

A few of the many embodiments encompassed by the present description are summarized in the following numbered paragraphs. The numbered paragraphs are self-referential. In this regard, it is explicitly applicant's purpose in setting forth the following paragraphs to describe various aspects and embodiments particularly by the paragraphs taken in combination. That is, the paragraphs are a compact way of setting out and providing explicit written description of all the embodiments that are encompassed by them individually and in combination with one another and, accordingly, applicant specifically reserves the right at any time to claim any subject matter set out in any of the following paragraphs, alone or together with any other subject matter of any one or more other paragraphs, including any combination of any values therein set forth taken alone or in any combination with any other value set forth. Should it be required, applicant specifically reserves the right to set forth all of the combinations herein set forth in full in this application or in any successor applications having benefit of this application.

Aspects of the invention are therefore (amongst others)

1.) A blood cell chemically coupled with at least five of the following eight immunodominant myelin peptides:
$MBP_{13-32}$, $MBP_{83-99}$, $MBP_{111-129}$, $MBP_{146-170}$, $PLP_{139-154}$, $MOG_{1-20}$, $MOG_{35-55}$ and $MBP_{82-98}$.

1a) A blood cell chemically coupled with at least five of the following twenty immunodominant myelin peptides:
$MBP_{13-32}$, $MBP_{83-99}$, $MBP_{111-129}$, $MBP_{82-98}$, $MBP_{82-99}$, $MBP_{82-106}$, $MBP_{87-106}$) $MBP_{131-155}$, $MBP_{146-170}$, $PLP_{41-58}$, $PLP_{89-106}$, $PLP_{95-116}$, $PLP_{139-154}$, $PLP_{178-197}$, $PLP_{190-209}$, $MOG_{1-20}$, $MOG_{11-30}$, $MOG_{21-40}$, $MOG_{35-55}$, $MOG_{64-86}$.

2) A blood cell chemically coupled with a cocktail containing six, seven or eight of the following eight immunodominant myelin peptides:
$MBP_{13-32}$, $MBP_{83-99}$, $MBP_{111-129}$, $MBP_{146-170}$, $PLP_{139-154}$, $MOG_{1-20}$, $MOG_{35-55}$ and $MBP_{82-98}$.

2a) A blood cell chemically coupled with a cocktail containing six, seven, eight or even more (up to 14) of the following twenty immunodominant myelin peptides:
$MBP_{13-32}$, $MBP_{83-99}$, $MBP_{111-129}$, $MBP_{82-98}$, $MBP_{82-99}$, $MBP_{82-106}$, $MBP_{87-106}$, $MBP_{131-155}$, $MBP_{146-170}$, $PLP_{41-58}$, $PLP_{89-106}$, $PLP_{95-116}$, $PLP_{139-154}$, $PLP_{178-197}$, $PLP_{190-209}$, $MOG_{1-20}$, $MOG_{11-30}$, $MOG_{21-40}$, $MOG_{35-55}$, $MOG_{64-86}$.

3) A blood cell chemically coupled with a cocktail of peptides, wherein the cocktail is selected from one of the cocktails a-d, defined above.

3a) A blood cell chemically coupled with a cocktail of peptides, wherein the cocktail is selected from one of the cocktails e-oo, defined above.

4.) A red blood cell (erythrocyte) chemically coupled with at least five of the following eight immunodominant myelin peptides:
$MBP_{13-32}$, $MBP_{83-99}$, $MBP_{111-129}$, $MBP_{146-170}$, $PLP_{139-154}$, $MOG_{1-20}$, $MOG_{35-55}$ and $MBP_{82-98}$.

4a) A red blood cell (erythrocyte) chemically coupled with at least five of the following twenty immunodominant myelin peptides:
$MBP_{13-32}$, $MBP_{83-99}$, $MBP_{111-129}$, $MBP_{82-98}$, $MBP_{82-99}$, $MBP_{82-106}$, $MBP_{87-106}$, $MBP_{131-155}$, $MBP_{146-170}$, $PLP_{41-58}$, $PLP_{89-106}$, $PLP_{95-116}$, $PLP_{139-154}$, $PLP_{178-197}$, $PLP_{190-209}$, $MOG_{1-20}$, $MOG_{11-30}$, $MOG_{21-40}$, $MOG_{35-55}$, $MOG_{64-86}$.

5) A red blood cell (erythrocyte) chemically coupled with a cocktail containing six, seven or eight of the following eight immunodominant myelin peptides:
$MBP_{13-32}$, $MBP_{83-99}$, $MBP_{111-129}$, $MBP_{146-170}$, $PLP_{139-154}$, $MOG_{1-20}$, $MOG_{35-55}$ and $MBP_{82-98}$.

5a) A red blood cell (erythrocyte) chemically coupled with a cocktail containing six, seven, eight or even more (up to 14) of the following twenty immunodominant myelin peptides:
$MBP_{13-32}$, $MBP_{83-99}$, $MBP_{111-129}$, $MBP_{82-98}$, $MBP_{82-99}$, $MBP_{82-106}$, $MBP_{87-106}$, $MBP_{131-155}$, $MBP_{146-170}$, $PLP_{41-58}$, $PLP_{89-106}$, $PLP_{95-116}$, $PLP_{139-154}$, $PLP_{178-197}$, $PLP_{190-209}$, $MOG_{1-20}$, $MOG_{11-30}$, $MOG_{21-40}$, $MOG_{35-55}$, $MOG_{64-86}$.

6) A red blood cell chemically coupled with a cocktail a cocktail of peptides, wherein the cocktail is selected from
a) $MBP_{13-32}$, $MBP_{83-99}$, $MBP_{111-129}$, $MBP_{146-170}$, $PLP_{139-154}$, $MOG_{1-20}$ and $MOG_{35-55}$
b) $MBP_{13-32}$, $MBP_{82-98}$, $MBP_{111-129}$, $MBP_{146-170}$, $PLP_{139-154}$, $MOG_{1-20}$ and $MOG_{35-55}$
c) $MBP_{13-32}$, $MBP_{83-99}$, $MBP_{111-129}$, $MBP_{146-170}$, $PLP_{139-154}$, $MOG_{1-20}$, $MOG_{35-55}$ and $MBP_{82-98}$
d) $MBP_{13-32}$, $MBP_{111-129}$, $MBP_{146-170}$, $PLP_{139-154}$, $MOG_{1-20}$ and $MOG_{35-55}$.

7.) A peripheral blood mononuclear cell chemically coupled with at least five of the following eight immunodominant myelin peptides:
$MBP_{13-32}$, $MBP_{83-99}$, $MBP_{111-129}$, $MBP_{146-170}$, $PLP_{139-154}$, $MOG_{1-20}$, $MOG_{35-55}$ and $MBP_{82-98}$.

8) A peripheral blood mononuclear cell chemically coupled with a cocktail containing six, seven or eight of the following eight immunodominant myelin peptides:
$MBP_{13-32}$, $MBP_{83-99}$, $MBP_{111-129}$, $MBP_{146-170}$, $PLP_{139-154}$, $MOG_{1-20}$, $MOG_{35-55}$ and $MBP_{82-98}$.

9) A peripheral blood mononuclear cell chemically coupled with a cocktail of peptides, wherein the cocktail is selected from selected from one of the cocktails a-d, defined above.

9a) A peripheral blood mononuclear cell chemically coupled with a cocktail of peptides, wherein the cocktail is selected from selected from one of the cocktails e-oo, defined above.

It has to be understood that in any of the aspects 1-9a described above the blood cells may be autologous or allogeneic in case of red blood cells (erythrocytes). It has to be further understood that in any of the aspects 1-9a described above the blood cells may be autologous in case of peripheral blood mononuclear cells (PBMCs).

BRIEF DESCRIPTION OF THE DRAWINGS

The patent or application filed contains at least one drawing executed in color. Copies of this patent or patent application publication with color drawing(s) will be provided by the Office upon request and payment of the necessary fee. Various features and advantages of the embodiments herein described can be fully appreciated as the same becomes better understood when considered in light of the accompanying drawings:

In FIG. 1, cells were pulsed in-vitro in the presence or absence of either biotin PLP, EDC or both. The top panel shows cells stained with Streptavidin Cy3. The middle panel shows a plot of streptavidin APC plotted against cell count. The bottom table describes the results of the experiment, in that the peptide on the surface of cells was only detected in the presence of both EDC and biotinPLP.

FIG. 2 shows the biotin peptide is efficiently bound to the cells during the manufacture process in bags. The top panel shows cells stained with Streptavidin Cy3. The middle panel shows a plot of streptavidin APC plotted against cell count. The open histogram shows PBMC after lysis, before the coupling reaction; the filled histogram shows the product (PBMC after coupling reaction).

Figure 1:
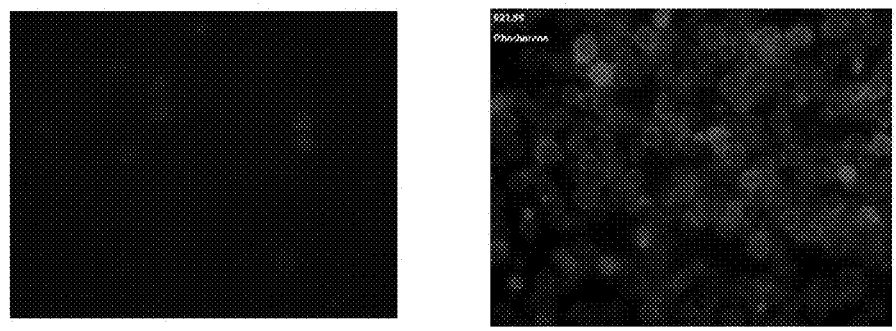
FIG. 1 and FIG. 2 together show results of two separate validation runs on the binding of the peptide to the surface of the cells, as detected by FACS and fluorescence microscopy using fluorophore conjugated streptavidin (Streptavidin-Cy3 and Streptavidin-APC respectively).
Figure 1:
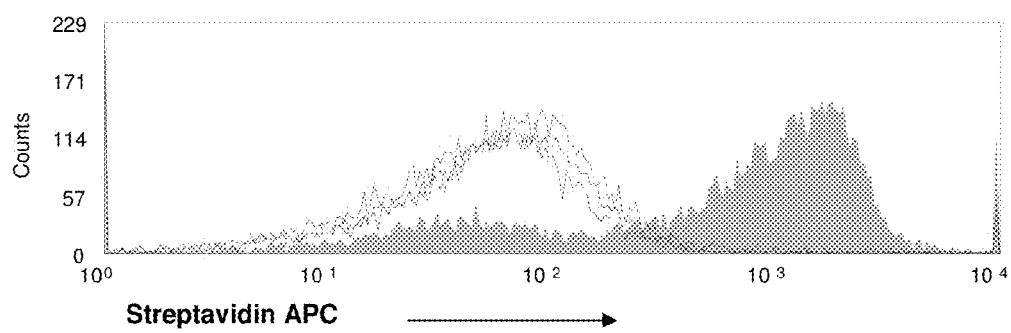

In an animal model of MS, experimental autoimmune encephalomyelitis (EAE), this protocol has shown dramatic therapeutic efficacy on clinical and pathological signs of disease. It not only silences the immune response against the major autoantigen, but also prevents epitope spreading to other myelin peptides within the same protein (intramolecularly) and also additional myelin proteins (intermolecularly), which represents an important advantage over other therapies. It is expected that treatment will decrease the average number of monthly contrast-enhancing MRI lesions by 50% or greater and reduce the number, change the phenotype of myelin peptide-specific T cells from a pro-inflammatory Th1/Th17 to an anti-inflammatory Th2-like type and/or render autoreactive T cells anergic.

Advantages of the protocol are: 1. Tolerance is exquisitely antigen-specific and therefore will not alter the normal immune response as do current immunosuppressive regimens. 2. From preclinical studies it was noted that in most cases a single intravenous infusion of peptide-pulsed peripheral blood mononuclear cells (PBMC) will induce long-term amelioration, which is a substantial improvement compared to all current therapies.

If needed, patients may be treated more than once in their life-time (they may be re-treated as needed e.g. on a yearly basis). 3. Tolerance is inducible in both naïve and activated Th1 cells. It is considered safer and more effective than tolerance induced by peripheral administration of soluble peptide or DNA vaccination with myelin peptide, which are both currently in phase II and -III clinical testing.

MS and role of T cells: Current evidence suggests CD4+ autoreactive T cells as a central factor for the autoimmune pathogenesis of MS probably relevant not only for the induction and maintenance of the autoimmune response, but also during tissue damage (Sospedra and Martin 2005, Annu. Rev. Immunol. 23:683). The frequency of activated CD4+ T cells reactive to main constituents of the myelin sheath, such as myelin basic protein (MBP), proteolipid protein (PLP) and myelin oligodendrocyte glycoprotein (MOG) is increased in MS patients. The instant application further demonstrates that high avidity myelin-specific T cells, which derive from the memory T cell pool and preferentially express a Th1 cytokine phenotype, are clearly more frequent in MS patients than in controls (Bielekova et al. 2004, J. Immunol. 172:3893). Due to their pathogenetic involvement CD4+ T cells are one logical target for therapeutic interventions. Tolerization by peptide-pulsed, fixed APC in the animal model of MS: Many pathological characteristics of human MS are reflected in the situation of EAE, a paradigmatic model of Th1/Th17 cell-driven autoimmune disease. Studies in relapsing EAE (R-EAE) in the SJL mouse have clearly shown that chronic demyelination involves the activation of T cell responses to multiple endogenous antigens arising via epitope spreading (Vanderlugt and Miller 2002, Nat. Rev. Immunol 2:85). Unresponsiveness of T cells can be induced when antigen presenting cells (APC) pulsed with antigenic peptide are treated with the cross linker 1-ethyl-3-(3-dimethylaminopropyl)-carbodiimide (ECDI, sometimes also referred to as EDC).

A still further aspect of the invention is a peripheral blood mononuclear cell as described above in which the chemical coupling is achieved by 1-ethyl-3-(3-dimethylaminopropyl)-carbodiimide (ECDI) which is preferred over other possible coupling agents.

Preclinical experiments have proven that a single i.v. injection of naïve murine splenocytes pulsed with a mixture of encephalitogenic myelin peptides and fixed with the cross linker ECDI is highly efficient in inducing peptide-specific tolerance in vivo. In EAE this protocol not only prevented animals from disease but even effectively reduced the onset and severity of all subsequent relapses when given after disease induction, indicating that specific tolerance can down regulate an ongoing autoimmune response (Kohm and Miller 2005, Int. Rev. Immunol. 24:361). More relevant to the treatment of MS, studies in EAE have shown that tolerance can be simultaneously induced to multiple epitopes using a cocktail of encephalitogenic myelin peptides, thus providing the capacity to target autoreactive T cells with multiple specifities. This regimen of antigen-specific peripheral tolerance is superior to tolerance induction by oral, subcutaneous or intraperitoneal administration of antigen and has also proven to be safe and effective in other experimental models of different T cell driven autoimmune diseases and in allograft rejection. Tolerization of human T cells by autologous antigen-coupled APCs treated with ECDI is effective in vitro as shown by failure of tolerized T cells to proliferate or to produce Th1 cytokines and a decreased expression of costimulatory molecules on these cells (Vandenbark et al. 2000, Int. Immunol. 12:57). There is evidence that at least two distinct mechanisms are involved in the induction of antigen specific tolerance by this regime. 1) Direct tolerance where Th1 clones encountering nominal antigen/MHC complexes on chemically-fixed APCs were anergized as a result of failure to receive adequate CD28-mediated costimulation (Jenkins and Schwartz. 1987, J. Exp. Med. 165:302) and 2) an indirect mechanism (cross tolerance) where tolerance is induced by reprocessing and re-presentation of antigens by host APCs (Turley and Miller, 2007, J. Immunol 178:2212). Treatment of cells with ECDI induces apoptosis in a substantial percentage of treated cells. Thus an indirect mechanism that involves fixed APC undergoing apoptosis, which are then processed and represented by host APC, is likely. This is further supported by effective induction of tolerance in MHC deficient and allogeneic mice. In-vitro bone marrow derived dendritic cells effectively phagocyte and process antigen pulsed, fixed APC. Choice of Peptides for Tolerization: Based on the rationale that T cells that recognize myelin peptides with high functional avidity might be most relevant for the autoimmune process in MS, embodiments of the present application provide high avidity myelin-specific T cells and employed 20 myelin peptides derived from MBP, PLP and MOG (Bielekova et al. 2004, J. Immunol. 172:3893). In summary these studies showed the following: (1) high avidity myelin-specific T cells are clearly more frequent in MS patients than in controls; (2) most of these T cells are derived from the memory T cell pool, and (3) express a Th1 cytokine phenotype; (4) only myelin epitopes $MBP_{13-32}$, $MBP_{111-129}$, $MBP_{146-170}$, $PLP_{139-154}$, $MOG_{1-20}$ and $MOG_{35-55}$ contributed to the increased reactivity observed in MS patients and (5) each those peptides against which high avidity T cells are mainly directed, is predicted as a poor binder to the main MS-associated HLA-DR alleles, which indicates that myelin peptides that bind poorly to MS-associated DR alleles are less likely to induce negative selection in the thymus. It should be noted that MBP $peptide_{83-99}$ will be included because this peptide has been shown to be immunodominant in MS patients by many prior studies.

Antigen-Coupled Cell Tolerance in Humans—the ETIMS Approach

A first—in-man trial (ETIMS trial) was conducted in MS patients with the aim to assess the feasibility, safety and tolerability of this novel tolerization regimen, which employs a single infusion of autologous peripheral blood mononuclear cells chemically coupled with seven myelin peptides ($MOG_{1-20}$, $MOG_{35-55}$, $MBP_{13-32}$, $MBP_{83-99}$, $MBP_{111-129}$, $MBP_{146-170}$ and $PLP_{139-154}$). In the open-label, single center, dose escalation study, nine MS patients (7 relapsing-remitting and 2 secondary progressive; EDSS 1-5.5), who were off-treatment for standard therapies were treated with a single infusion of ETIMS product. All patients had to show T cell reactivity against at least one of the myelin peptides used in the trial. Neurological, MRI, laboratory and immunological examinations were performed to assess the safety, tolerability and in vivo mechanisms of action of this regimen. Overall, administration of antigen-coupled cells was feasible, had a favorable safety profile and was well tolerated in MS patients. Compared to the pre-treatment observation period there was no increase in clinical and MRI parameters of disease activity by this regimen. Patients receiving the high dose ($>1\times10^9$) of peptide-coupled cells showed a decrease in antigen-specific T cell responses following ETIMS therapy (Lutterotti et al. 2013).

Further aspects of the invention therefore include:

10) A pharmaceutical composition containing blood cells as described herein for systemic administration.
11) A pharmaceutical composition containing blood cells as described herein for i.v. administration.
12) A medical product containing at least one cell as described herein.
13) The use of cells as described herein for the manufacture of a medicament for the treatment of MS.
14.) The use of cells as described herein for the manufacture of a medicament for the treatment of MS, characterized in that the cells are allogeneic cells.
15) The use of cells as described herein for the manufacture of a medicament for the treatment of MS, characterized in that the cells are autologous cells.
16) A method of treating patients suffering from MS by systemic administration of a pharmaceutical composition containing blood cells coupled with a cocktail of peptides as described herein.

ETIMS is a cell-based tolerization therapy that involves autologous antigen-presenting cells pulsed with a specific set of myelin peptides in the presence of a chemical coupling agent. This therapy is in many aspects novel and unique. These include a) the use of a set of peptides that covers the immunodominant epitopes of those myelin proteins, which are targeted by the high-avidity autoimmune T cell response in MS, b) different from all other tolerization therapies, ETIMS was shown to prevent epitope spreading, i.e. the broadening of the autoimmune response to other target epitopes, c) based on extensive animal testing, ETIMS is expected to be safer and more effective than those tolerization therapies that are currently in clinical testing in MS, i.e. administration of a single soluble peptide intravenously by BioMS and intramuscular administration of a plasmid encoding a myelin peptide together with a Th2 cytokine by Bayhill Pharmaceuticals, d) it was contemplated that only a single treatment is required, which represents a major advantage with respect to patient acceptance.

The specificity, lack of side effects, and single time administration are considered major advantages of this treatment.

The scientific strategy follows two major goals: 1. To establish the efficacy and safety of ETIMS as a tolerizing treatment in early MS, and 2. To establish the precise in vivo mechanism of action of ETIMS. These mechanistic studies will include the exploration of more selective cell populations for tolerization, e.g. immature dendritic cells, B cells, others, in order to improve both efficacy and our intellectual property position.

Ideally peptide specific immune tolerance should be achieved early in the inflammatory phase of the disease, where blockade of the autoreactive immune response can inhibit dissemination and propagation of the disease and irreversible disability can be prevented. Therefore the targeted patient group are relapsing-remitting MS patients early in the disease course or even patients presenting with a first clinical event suggestive of MS, i.e. clinically isolated syndromes (CIS). At this time point MS patients generally have a low grade of neurologic disability, which allows them to participate in all activities of daily life and work without significant compromise.

One further aspect of the invention is a medicinal product for human use (ETIMS) containing blood cells that have been pulsed with at least five of eight immunodominant myelin peptides ($MBP_{13-32}$, $MBP_{83-99}$, $MBP_{111-129}$, $MBP_{146-170}$, $PLP_{139-154}$, $MOG_{1-20}$, $MOG_{35-55}$ and $MBP_{82-98}$) and fixed with the cross-linker ECDI. Preferred blood cells are red blood cells, more preferred blood cells are peripheral blood mononuclear cells (PBMC). The blood cells may be autologous or allogeneic.

Another further aspect of the invention is a medicinal product for human use (ETIMS) containing blood cells that have been pulsed with at least five of twenty immunodominant myelin peptides ($MBP_{13-32}$, $MBP_{83-99}$, $MBP_{111-129}$, $MBP_{82-98}$, $MBP_{82-99}$, $MBP_{82-106}$, $MBP_{87-106}$, $MBP_{131-155}$, $MBP_{146-170}$, $PLP_{41-58}$, $PLP_{89-106}$, $PLP_{95-116}$, $PLP_{139-154}$, $PLP_{178-197}$, $PLP_{190-209}$, $MOG_{1-20}$, $MOG_{11-30}$, $MOG_{21-40}$, $MOG_{35-55}$, $MOG_{64-86}$) and fixed with the cross-linker ECDI. Preferred blood cells are red blood cells, more preferred blood cells are peripheral blood mononuclear cells (PBMC). The blood cells may be autologous or allogeneic.

A preferred aspect of the invention is a medicinal product for human use (ETIMS) containing blood cells that have been pulsed with six, seven or eight of eight immunodominant myelin peptides ($MBP_{13-32}$, $MBP_{83-99}$, $MBP_{111-129}$, $MBP_{146-170}$, $PLP_{139-154}$, $MOG_{1-20}$, $MOG_{35-55}$ and $MBP_{82-98}$) and fixed with the cross-linker ECDI. Preferred blood cells are red blood cells, more preferred blood cells are peripheral blood mononuclear cells (PBMC). The blood cells may be autologous or allogeneic.

A further preferred aspect of the invention is a medicinal product for human use (ETIMS) containing blood cells that have been pulsed with six, seven, eight or even more (up to 14) of twenty immunodominant myelin peptides ($MBP_{13-32}$, $MBP_{83-09}$, $MBP_{111-129}$, $MBP_{82-98}$, $MBP_{82-99}$, $MBP_{82-106}$, $MBP_{87-106}$, $MBP_{131-155}$, $MBP_{146-170}$, $PLP_{41-58}$, $PLP_{89-106}$, $PLP_{95-116}$, $PLP_{139-154}$, $PLP_{178-197}$, $PLP_{190-209}$, $MOG_{1-20}$, $MOG_{11-30}$, $MOG_{21-40}$, $MOG_{35-55}$, $MOG_{64-86}$) and fixed with the cross-linker ECDI. Preferred blood cells are red blood cells, more preferred blood cells are peripheral blood mononuclear cells (PBMC). The blood cells may be autologous or allogeneic.

An even more preferred aspect of the invention is a medicinal product for human use (ETIMS) containing blood cells that have been pulsed with a cocktail of peptides according to the foregoing and the following aspects, wherein the cocktail is selected from one of the cocktails a-d or e-oo, defined above, and fixed with the cross-linker ECDI. Preferred blood cells are red blood cells (erythrocytes), more preferred blood cells are peripheral blood mononuclear cells (PBMC). The blood cells may be autologous or allogeneic.

The safety, preliminary efficacy and in vivo mechanisms of action of ETIMS in early relapsing remitting MS patients can be demonstrated in a clinical trial.

Manufacture Process:

The manufacturing process for the blood cells according to the invention is described below by way of example. It has to be understood that this description is not limiting in any way. An expert in the art is able to adapt the example to specific needs without any need to be inventive. The description below is in particular easily adaptable to other types of blood cells.

The excipients erythrocyte lysis buffer and peptide solution may be produced in advance and stored at $<-20°$ C.

Peptide Solution

The peptide solution is prepared in the clean room (Category A) in the Department of Transfusion Medicine. First, 30 (±3) mg of each single peptide are weighed in and solved in 7.5 ml of water for injections (final concentration of peptide 4 mg/ml), respectively. Thereafter all peptides are pooled by transferring 5 ml of each single-peptide solution into a new tube and adding 5 ml of water for injections (total volume 40 ml) to obtain a final concentration of 0.5 mg/ml of each single peptide. Peptide-pool solution may be aliquoted in 1.5 ml aliquots (20 aliquots) in sterile and endotoxin free NUNC Cryo Tube vials (NalgeNunc International) and stored at $-20°$ C. until use or may be used directly in the manufacturing process. 5 ml of the Peptide-pool solution are transferred into a blood-bag containing 30 ml of water for injections for sterility testing. 5 ml are aliquoted at 1 ml and stored at $-20°$ C. for later quality controls. Frozen peptide-pool solutions have to pass sterility control before they can be used in the manufacture process. The identity and presence of each single peptide in the pool may be verified. The maximum storage time is 3 months.

At the day of manufacture of drug product, 1 ml of peptide-solution is transferred to a blood bag (P1459, Fresenius; see IMPD 2.1.P.3.5 *Filling of blood bags in clean room*). The procedure is done in the clean room (category A). The blood bag containing the peptide solution is stored at $4°$ C. until use.

Erythrocyte Lysis Buffer

The preparation of the erythrocyte lysis buffer is done in the clean room. Briefly, 4 g of Ammonium chloride EMPROVE® Ph Eur and 0.5 g of Potassium hydrogen carbonate EMPROVE® Ph Eur are solved in 50 ml of water for injection (Ph Eur). Using a 50 ml syringe 25 ml of the solved lysing buffer are transferred to a blood bag through a sterile filter (0.2 μm, Millipore). The blood bag is filled up to 200 ml with water for injection and stored at $-20°$ C. until use. Two bags are filled. 50 ml of lysis buffer are transferred to a blood bag for sterility testing and 50 ml are preserved at $-20°$ C. for later quality control. Erythrocyte lysis buffer solutions have to pass sterility control before they can be used in the manufacture process. The maximum storage time is three months.

CPD/Saline Washing Solution

At the day of the manufacture process a CPD bag (Compoflex, Fresenius) containing 63 ml of CPD will be filled up to 500 ml with sterile physiologic saline (NaCl 0.9%, Baxter) solution. Bags will be connected by TSCD. A balance (PC4000, Mettler) is used to control for weight (500 g). Two bags are produced. At the end of the manufacture process residual washing solution is tested for sterility.

EDC Solution

In the clean room (Cat. A) 200 mg EDC are solved in 2 ml of water for injection. Using a sterile syringe 1 ml is transferred to a blood bag (P1459, Fresenius). The blood bag with the EDC solution is stored at $4°$ C. until use. Residual EDC is tested for sterility.

Collection of PBMC and Plasma

At the day of blood collection $2.5-5\times10^9$ PBMC will be isolated from study-qualifying MS patients by standard leukapheresis, performed according to policies and procedures at the Department of Transfusion Medicine. For the collection of cells, a standardized automatic program (AutoPBSC) on a Cobe Spectra apheresis machine (Cobe Spectra) was used. The AutoPBSC processes 4500 ml of blood and enriches PBMC in 6 harvest phases with approximately 10 ml volume each. In parallel to the collection of cells, 120 ml of autologous plasma will be collected during the apheresis procedure and stored at 4° C. in a standard blood bag. During the whole apheresis procedure ACD-A (Baxter) is used as anticoagulant to prevent clotting of blood. The AutoPBSC program uses ACD-A at 0.083 ml/ml (relation 1:12), however the amount can be adapted within defined ranges (0.071-0.1 ml/ml), if necessary. At the end of the apheresis the concentration of ACD-A in the cell product and plasma is documented in the production log.

Cell Processing

All steps described here are done maintaining a closed system. In practice excipients are pre-filled in blood bags in the clean room (category A) and added to the cells by connecting the bags using a sterile tubing welder (TSCD®, Terumo). The apheresate is transferred to a standard blood bag (Compoflex P1461 500 ml, Fresenius) by welding the tubes of the bags with the TSCD®. A small retention sample is maintained in the original blood bag that will be used for counting of cells after bags have been separated using a portable tubing sealer (Fresenius NBPI). Next, cells are separated from plasma by centrifugation at 300×g for 15 min at room temperature (RT). Plasma is removed from the bag by pressing it to a sterile connected empty bag, using a plasma extractor (Baxter). The bags are separated by a portable tubing sealer. To lyse erythrocytes the bag containing the erythrocyte lysing buffer (ACK) is connected by the TSCD and the cell pellet is resuspended in 200 ml erythrocyte lysis buffer and incubated for 15 min, RT, shaking (3 rpm) on a wave platform shaker (Heidolph). At the end of the incubation period cells are washed with 200 ml CPD 12.6%/saline and centrifuged for 15 min at 200 g at 4° C. Supernatant is removed from the bag by pressing it to an empty bag, using a plasma extractor. The cells are washed again with 200 ml CPD 12.6%/saline. Cells are centrifuged for 15 min at 200 g at 4° C. and supernatant is removed from the bag. Cells are transferred to a 150 ml bag (Compoflex 1459, Fresenius) and a retention sample is taken for cell counting. $1.5$-$7 \times 10^9$ PBMC will be re-suspended in 20 ml saline and 1 ml peptide-pool solution containing 0.5 mg/ml of each GMP manufactured peptide added. The selected peptides (e.g. MBP1, MBP2, MBP3, MBP4, PLP1, MOG1 and MOG2) will be used for coupling. The coupling reaction is initiated by the addition of 1 ml of 100 mg/ml of freshly prepared water-soluble 1-ethyl-3-(3-dimethylaminopropyl-)-carbodiimide (EDC). Following 1 h incubation shaking at 4° C., the peptide-coupled cells are washed 2 times with 100 ml CPD/saline and finally re-suspended in autologous plasma at a concentration given by the specification ($1 \times 10^6$, $1 \times 10^6$ or $1 \times 10^7$ cells/ml). At this time sample is taken for release testing prior to infusion. Cells will be carefully checked for the absence of clumping. 100 ml of final ETIMS cell product will be infused using a standard blood transfusion kit with inline-filter (200 μm). The control of critical steps and intermediates are described in IMPD 2.2.P.3.4 and the flow chart (IMPD FIG. 2.1.P.3.3 1-3).

The whole manufacture process is performed within standard blood bags in a functionally closed system. In practice peptides, lysis buffer and washing solutions are filled in standard blood bags under sterile and endotoxin free conditions in a licensed clean room laboratory (category A, ISO14644 certified)) following strict GMP standards at Department of Transfusion Medicine. In the manufacture process the addition of these materials/reagents are carried out by welding the tubes of the respective blood bags with a sterile tubing welder (Terumo TSCD®).

The most preferred coupling agent for the process described above is by 1-ethyl-3-(3-dimethylaminopropyl)-carbodiimide (ECDI) as described above. However, other coupling agents (e.g. based on different carbodiimides) do qualify as well.

Further aspect of the invention therefore are:

17) A process for the manufacture of a peripheral blood mononuclear coupled with at least five of the following eight immunodominant myelin peptides:
   $MBP_{13-32}$, $MBP_{83-99}$, $MBP_{111-129}$, $MBP_{146-170}$, $PLP_{139-154}$, $MOG_{1-20}$, $MOG_{35-55}$ and $MBP_{82-98}$,
   containing the steps of isolating peripheral blood mononuclear cells, adding the selected peptides and subsequent adding of the coupling agent.

17a) A process for the manufacture of a peripheral blood mononuclear coupled with at least five of the following twenty immunodominant myelin peptides:
   $MBP_{13-32}$, $MBP_{83-99}$, $MBP_{111-129}$, $MBP_{82-98}$, $MBP_{82-99}$, $MBP_{82-106}$, $MBP_{87-106}$, $MBP_{131-155}$, $MBP_{146-170}$, $PLP_{41-58}$, $PLP_{89-106}$, $PLP_{95-116}$, $PLP_{139-154}$, $PLP_{178-197}$, $PLP_{190-209}$, $MOG_{1-20}$, $MOG_{11-30}$, $MOG_{21-40}$, $MOG_{35-55}$, $MOG_{64-86}$,
   containing the steps of isolating peripheral blood mononuclear cells, adding the selected peptides and subsequent adding of the coupling agent.

18) A process for the manufacture of a peripheral blood mononuclear coupled with six or seven or eight of the following eight immunodominant myelin peptides:
   $MBP_{13-32}$, $MBP_{83-99}$, $MBP_{111-129}$, $MBP_{146-170}$, $PLP_{139-154}$, $MOG_{1-20}$, $MOG_{35-55}$ and $MBP_{82-98}$,
   containing the steps of isolating peripheral blood mononuclear cells, adding the selected peptides and subsequent adding of the coupling agent.

18a) A process for the manufacture of a peripheral blood mononuclear coupled with six or seven, eight or even more (up to 14) of the following eight immunodominant myelin peptides:
   $MBP_{13-32}$, $MBP_{83-99}$, $MBP_{111-129}$, $MBP_{82-98}$, $MBP_{82-99}$, $MBP_{82-106}$, $MBP_{87-106}$, $MBP_{131-155}$, $MBP_{146-170}$, $PLP_{41-58}$, $PLP_{89-106}$, $PLP_{95-116}$, $PLP_{139-154}$, $PLP_{178-197}$, $PLP_{190-209}$, $MOG_{1-20}$, $MOG_{11-30}$, $MOG_{21-40}$, $MOG_{35-55}$, $MOG_{64-86}$,
   containing the steps of isolating peripheral blood mononuclear cells, adding the selected peptides and subsequent adding of the coupling agent.

19) A process for the manufacture of a peripheral blood mononuclear coupled with at least five of the following eight immunodominant myelin peptides:
   $MBP_{13-32}$, $MBP_{83-99}$, $MBP_{111-129}$, $MBP_{146-170}$, $PLP_{139-154}$, $MOG_{1-20}$, $MOG_{35-55}$ and $MBP_{82-98}$,
   in which the coupling agent is ECDI.

19a) A process for the manufacture of a peripheral blood mononuclear coupled with at least five of the following eight immunodominant myelin peptides:
   $MBP_{13-32}$, $MBP_{83-99}$, $MBP_{111-129}$, $MBP_{82-98}$, $MBP_{82-99}$, $MBP_{82-106}$, $MBP_{87-106}$, $MBP_{131-155}$, $MBP_{146-170}$, $PLP_{41-58}$, $PLP_{89-106}$, $PLP_{95-116}$, $PLP_{139-154}$, $PLP_{178-197}$, $PLP_{190-209}$, $MOG_{1-20}$, $MOG_{11-30}$, $MOG_{21-40}$, $MOG_{35-55}$, $MOG_{64-86}$,
   in which the coupling agent is ECDI.

It has to be understood that in any of the aspects 17-19 described above the blood cells may be autologous or allogeneic.

Validation of the Manufacture Process

Validation of Infrastructure and Technical Equipment

Several validation runs arte to be performed to assure that the infrastructure and the technical equipment are suitable for the manufacture process. The collection of cells will be performed in a apheresis unit such as the Department for Transfusion Medicine, UKE (see also Validation of leukapheresis) following SOPs. Cells will be processed in a Clean room. Washing, centrifugation and incubation steps will be done in a clean room Category D (Room 29) while maintaining a closed system. The system will be opened only in the clean room category A. All procedures will be performed by trained personnel only.

All technical equipment used for the processing of cells is certified for its intended use and maintained following SOP's. Only material that has passed the Quality control will be used.

Validation of Leukapheresis

Validation of the apheresis protocol and the characterisation of the cell product were done with aphereses from healthy donors and MS patients. All Aphereses were run on a CobeSpectra apheresis machine at the Department for Transfusion Medicine, UKE. The AutoPBSC program has been selected for several reasons (Table 1). 1) By processing a standardized blood volume (4500 ml), a sufficient yield of cells was obtained. 2) The cell product has a high purity of mononuclear cells in a standardized volume of the cell product. 3) Compared to the manual program the erythrocyte count is lower.

a sterile welding device. After the reagents have been filled in the bag, the tube will be separated using a portable tubing sealer.

Cell Number

The absolute cell number in the product is a critical point in the manufacture process. During the manufacture process cells are lost (Table 3). Thus it is essential to define minimal cell numbers that are required for the production of the ETIMS product. These cell numbers have to be checked through in-process controls. The acceptance criteria for the cell numbers necessary for the manufacture process have been defined in several validation runs using buffy coats. The cell content of buffy coat is approximately $1 \times 10^9$ cells, thus for the validation runs a final cell number of $5 \times 10^8$ cells was targeted. Cell counts were assessed before starting the manufacture process, before the coupling reaction and after the last washing step. In all validation runs the target cell count could be reached, when the initial cell number was higher than $1.2 \times 10^9$.

TABLE 1

| | ApheresisDuration (min) | Blood Volume (ml) of patient | Product Volume (ml) | PBMC × $10^9$ | % lymphocytes (within MNC) | % monocytess (within MNC) |
|---|---|---|---|---|---|---|
| 290SA | 128 | 4500 | 61 | 5.5 | 77.6 | 17.8 |
| IJ1804 | 86 | 4552 | 61 | 5.1 | 80.2 | 13.4 |
| 445CO | 88 | 3908 | 61 | 5.5 | 67.7 | 15.2 |
| 978TH | 99 | 5502 | 61 | 5.5 | 62.4 | 21.5 |
| RM1401 | 102 | 5153 | 60 | 4.2 | 71.0 | 22.8 |
| IJ2801 | 115 | 5747 | 60 | 2.7 | 82.6 | 10.8 |
| 1066ST | 112 | 3479 | 61 | 5.5 | 72.9 | 16.7 |

Validation of Erythrocyte Lysis

Although the apheresis product contains a very low number of erythrocytes, in absolute numbers erythrocytes outweigh mononuclear cells 10 to 40 times. Thus it is necessary to lyse erythrocytes to obtain a higher purity of the cell product. For the lysis of erythrocytes an established lysis buffer (ACK-buffer) was used. The efficiency of the lysis buffer in buffy coats, which contain a much higher amount of erythrocytes compared to apheresate, was tested. In buffy coat, efficient lysis of erythrocytes (mean hemoglobin (Hb) before lysis 10.03 g/dl, after lysis 0.63 g/dl; Table 2) was achieved. In aphereses the content of erythrocytes is much lower from the beginning and is below measurable values after lysis.

TABLE 2

| Product | Hb before lysis (g/dl) | Hb after lysis (g/dl) |
|---|---|---|
| BC9198169 | 8.4 | 0.4 |
| BC9204876 | 12.6 | 1.0 |
| BC9247719 | 9.8 | 0.5 |
| BC9261124 | 9.32 | 0.6 |

Filling of Blood Bags in Clean Room

All reagents will be filled through a sterile tube which has a Luer-lock device. The tube will be welded to the bag using

TABLE 3

| Buffy coat | Duration (min) | Initial Cell count | Cell count after lysis | Cell count after coupling |
|---|---|---|---|---|
| 9261124 | 320 | $16.5 \times 10^8$ | $9.95 \times 10^8$ | $7.2 \times 10^8$ |
| 9247719 | 330 | $17 \times 10^8$ | $11 \times 10^8$ | $6.5 \times 10^8$ |
| 9204876 | 380 | $15 \times 10^8$ | $11.4 \times 10^8$ | $10 \times 10^8$ |
| 9198169 | 350 | $12 \times 10^8$ | $8.6 \times 10^8$ | $11 \times 10^8$ |

Duration of Manufacture Process

An aim was to reduce the duration of the manufacture process in order to enhance viability and lower the risk of microbiological contamination. Since in several validation runs residual amounts of EDC could not be detected in the first washing solution after the coupling reaction, a washing step after the lysis of erythrocytes and one after the coupling reaction was reduced. This led to a reduction of the manufacture process of approximately 57 minutes. The reduction of the duration of the manufacture process was paralleled by an increase in cell viability measured as membrane integrity by FACS-Analysis (Ph Eur 2.7.29). The mean duration is 292 min (Table 4).

TABLE 4

| Product | Duration (min) | Initial Cell count | Cell count after lysis | Cell count after coupling |
|---|---|---|---|---|
| RM1401 | 295 | $2 \times 10^9$ | $1.4 \times 10^9$ | $1.2 \times 10^9$ |
| IJ2801 | 295 | $2.5 \times 10^9$ | $2.2 \times 10^9$ | $1.8 \times 10^9$ |
| 9373085 | 285 | $1.3 \times 10^9$ | $1.0 \times 10^9$ | $0.8 \times 10^9$ | pH

The mean pH in the product after resuspension in human plasma was pH 7.7 (range 7.6-7.8; n=8). Autologous plasma was used in validation runs with apheresate and third party plasma matched for blood group in validation runs with buffy coat. pH was measured in supernatants of washing steps. The pH of lysis buffer is pH 7.4 the pH of the CPD buffer is pH 5.8.

Viability

Cell viability was assessed by measuring membrane integrity by Trypan blue exclusion and FACS (Ph.Eur. 2.7.29) at different time-points and storage conditions. (see IMPD 2.1.P.8).

Peptide Binding

An objective of the study was to evaluate whether efficient coupling of peptides to the surface of PBMC could be achieved in the manufacture process in bags.

Figure 2:
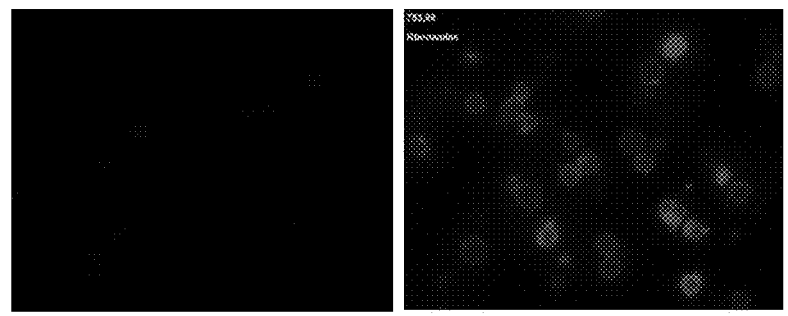
Figure 2:
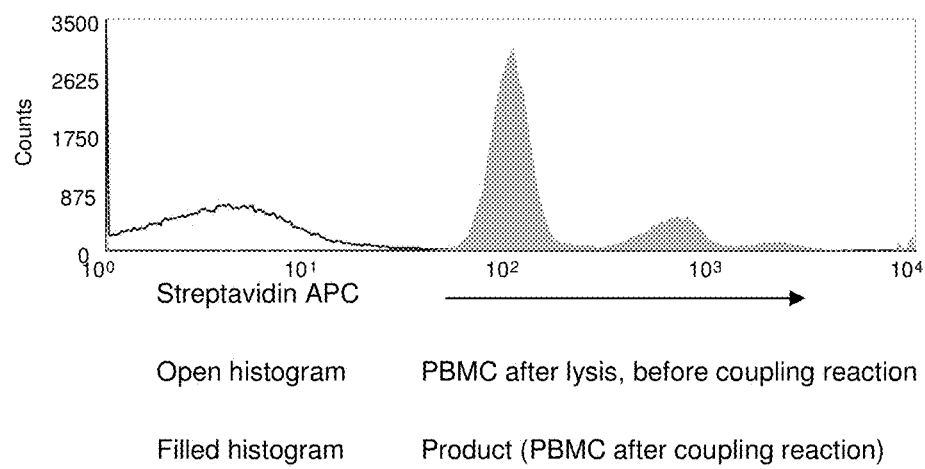

In-vitro it was demonstrated that the presence of both EDC and peptide is necessary for efficient binding of peptide to the cell surface (FIG. 2.1.P.3.5-1). To assess the efficiency of the coupling reaction in the manufacture process in bags, one of the seven peptides ($PLP_{139-154}$) has been replaced by a biotinylated peptide (biotin$PLP_{139-154}$). Binding of the peptide to the surface of the cells has been detected by FACS and fluorescence microscopy using fluorophore conjugated streptavidin (Streptavidin-Cy3 and Streptavidin-APC respectively). In the present study, using two separate validation runs, it was demonstrated that the peptide is binding efficiently to the surface of PBMC during the manufacture process in bags. One result representative of 2 independent validation runs is for example shown in FIG. 1.

Since the volume for the coupling reaction might vary (target volume 10 ml), the efficiency of the coupling procedure was assessed in 4 different volumes. At a concentration ranging for PBMC: $1 \times 10^7$-$0.33 \times 10^7$ cells/ml; for EDC: 100 mg/ml-33 mg/ml and for peptide-pool at 0.05 mg/ml-0.017 mg/ml peptide the binding is efficient. Further reduction of the concentration reduces the binding efficiency below accepted levels. Thus a volume range of 10-20 ml for the coupling procedure is acceptable.

Sterility

Sterility was maintained in 5 independent validation runs. Samples were tested for aerobial and anaerobial bacteria and fungi.

Endotoxin

Final washing solutions of 3 validation runs were tested for the presence of endotoxins (Pyrogene®, Lonza). Endotoxin (<0.5 EU/ml) could not be detected in the supernatant of the last washing solution before resuspension of cells in autologous plasma. The presence of endotoxins cannot be assessed in human plasma, since plasma inhibits the test.

Aggregates

Several measures were taken to ensure against the presence of aggregates.

a) Aggregates were not observed by visual inspection in any of the products in the validation runs (n=14). The infusion on the bench was stimulated with the blood transfusion kit with an inline filter (200 µm) that will be used for patients. Aggregates were not observed in the filter after having passed the cells. To further ensure against aggregates, the cell concentration was counted before and after having passed through the filter and yet no differences were observed (n=2).

b) The presence of aggregates was assessed by microscopy in a blood smear or after transferring cells to a cell culture plate. No differences were observed in the cells compared to non-treated cells.

c) In order to detect and quantify micro-aggregates several products (n=5) were analyzed by FACS. Measurement of the forward scatter area (FSC-A) and the forward scatter width (FSC-W) did not reveal a higher frequency of micro-aggregates in the cell product compared to the cells before EDC treatment. The frequency of aggregates did not increase during the storage period of 4 h.

d) Injection of human product (ETIMS) in mice (n=20) did not lead to embolism, because of aggregates in any of the mice.

Identity

The cellular composition of the apheresate and the final drug product was analyzed with the objective to evaluate differences in the final cellular composition of the drug product resulting from the processing of the cells. A clear phenotypic characterisation of the final product is hampered by the treatment of the cells, most probably because the chemical treatment alters the target structure for the specific antibodies. Thus, the cell product ias to be phenotyped before the processing of the cells in order to assess whether the relation between different populations (T cells, B cells, monocytes) have an influence on the treatment outcome. The aim is to establish acceptance criteria for the further development of the drug product.

Pre-clinical Safety

Animal studies: Two different experimental settings were used for the assessment of toxicity. 1) Toxicologic testing of the human product can only be assessed in the short term because of immunotoxicity when tested in different species. Thus the short term toxicity of the human product was assessed in immune-compromised mice (severe combined immunodeficiency; SCID). 2) Mid-term toxicity of syngeneic splenocytes coupled with the seven myelin peptides used in the trial was assessed in the SJL model.

Both toxicological studies were conducted by LPT Laboratory of Pharmacology and Toxicology GmbH & Co. KG, Redderweg, Hamburg, a GLP-certified laboratory.

Acute Toxicity Study of Human Peptide-coupled Peripheral Blood Mononuclear Cells (PBMC) and Human Plasma by Single Intravenous Administration to SCID Mice (LPT 22043).

| | |
|---|---|
| Test item | $1 \times 10^9$ Human PBMC chemically coupled to seven myelin peptides ($MBP_{13-32}$ (MBP1), $MBP_{83-99}$ (MBP2), $MBP_{111-129}$ (MBP3), $MBP_{146-170}$ (MBP4), $MOG_{1-20}$ |

| | |
|---|---|
| | (MOG1), $MOG_{35-55}$ (MOG2), $PLP_{139-154}$ (PLP1)) resuspended in 100 ml human plasma. Human plasma served as control |
| Number of experiments | Two different, at two independent time-points, manufactured human peptide-coupled PBMC (Product A and Product B) |
| Number of animals per experiment | 5 males and 5 females received peptide-coupled cells, 1 male and 1 female received human plasma as control |
| Intravenous injection | Dose/approx. 15 seconds |
| Administration volume | 200 μl i.v. |
| Dose | $2 \times 10^6$ peptide-coupled human PBMC |
| Body weight (at start of treatment) | |
| Males: | 17-22 g |
| Females: | 15-17 g |
| Age (at start of treatment) | |
| Males: | 41-48 days |
| Females: | 41-48 days |
| Identification of animal | By coloured marks and cage label |
| Duration of experiment | At least 5 adaptation days<br>1 test day<br>24 hours recovery period |
| Evaluation | Observations were performed for all animals and recorded systematically (with individual records being maintained for each animal) before and immediately, 5, 15, 30 and 60 min, as well as 3, 6 and 24 hours after administration. |
| Observation | Changes of skin and fur, eyes and mucous membranes, respiratory and circulatory function, autonomic and central nervous system and somatomotor activity as well as behaviour pattern were observed. Attention was also paid to possible tremor, convulsions, salivation, diarrhoea, lethargy, sleep and coma. Observations on mortality were made with appropriate actions taken to minimize loss of animals during the study. |
| Measurements | Individual body weights were recorded before administration of the test item and after 24 hours. Changes in weight were calculated and recorded. At the end of the experiments all animals were sacrificed under ether anaesthesesia by cutting the aorta abdominalis, exsanguinated, weighed, dissected and inspected macroscopically under the direction of a pathologist. |

Summarized Results

Under the present test conditions, single intravenous injections of 200 μL Human peptide-coupled peripheral PBMC (Product A), human peptide-coupled PBMC (Product B) or human plasma to mice did not lead to any signs of toxicity. No mortality occurred.

| Symptoms/Criteria | Product A | | Product B | | Human Plasma | |
|---|---|---|---|---|---|---|
| | males | females | males | females | males | females |
| Clinical signs | none | none | none | none | none | none |
| mortality within 6 h | 0 | 0 | 0 | 0 | 0 | 0 |
| within 24 h | 0 | 0 | 0 | 0 | 0 | 0 |
| Mean body weight start | 18.6 | 15.6 | 20.4 | 16.2 | 20.5 | 17.0 |
| after 24 h | 19.0 | 15.8 | 20.6 | 16.4 | 20.5 | 17.5 |
| Inhibition of body weight gain | none | none | none | none | none | none |
| Necropsy findings * | none | 2 of 5 | 4 of 5 | 4 of 5 | 2 of 2 | 2 of 2 |

* A reduced spleen size was observed in 0 of 5 male and 2 of 5 female animals treated with Product A, 4 of 5 male and 4 of 5 female animals treated with Product B and 2 of 2 male and 2 of 2 female animals treated with human plasma.

Acute Toxicity Study of Peptide Coupled Splenocytes by Single Intravenous Administration to SJL Mice (LPT 21988)

| | |
|---|---|
| Test item | Syngeneic splenocytes chemically coupled to seven myelin peptides ($MBP_{13-32}$ (MBP1), $MBP_{83-99}$ (MBP2), $MBP_{111-129}$ (MBP3), $MBP_{146-170}$ (MBP4), $MOG_{1-20}$ (MOG1), $MOG_{35-55}$ (MOG2), $PLP_{139-154}$ (PLP1)) resuspended in PBS. |
| Number of experiments | 1 |
| Number of animals per experiment | 5 males and 5 females received peptide-coupled splenocytes |

-continued

| | |
|---|---|
| Intravenous injection | Dose/approx. 15 seconds |
| Administration volume | 200 μl iv. |
| Dose | $5 \times 10^7$ peptide-coupled splenocytes |
| Body weight (at start of treatment) | |
| Males: | 17-19 g |
| Females: | 17-18 g |
| Age (at start of treatment) | |
| Males: | 43 days |
| Females: | 43 days |
| Identification of animal | By coloured marks and cage label |
| Duration of experiment | At least 5 adaptation days<br>1 test day<br>2 recovery weeks |
| Evaluation | Observations were performed for all animals and recorded systematically (with individual records being maintained for each animal) before and immediately, 5, 15, 30 and 60 min, as well as 3, 6 and 24 hours after administration. All animals were observed for a period of 14 days. |
| Observation | Changes of skin and fur, eyes and mucous membranes, respiratory and circulatory function. autonomic and central nervous system and somatomotor activity as well as behaviour pattern were observed. Attention was also paid to possible tremor. convulsions, salivation. diarrhoea, lethargy, sleep and coma. Observations on mortality were made at least once daily with appropriate actions taken to minimize loss of animals during the study. |
| Measurements | Individual body weights were recorded before administration of the test item and thereafter every day for the first three days followed by weekly intervals up to the end of the study. Changes in weight were calculated and recorded.<br>At the end of the experiments all animals were sacrificed under ether anaesthesesia by cutting the aorta abdominalis, exsanguinated, weighed, dissected and inspected macroscopically under the direction of a pathologist. |

Summarized Results

Under the present test conditions, a single intravenous injection of $5 \times 10^7$ peptide-coupled splenocytes to mice did not lead to any signs of toxicity. No mortality occurred. All animals gained the expected body weight throughout the whole study period.

| | | $5 \times 10^7$ cells/animal iv. n = 5 | |
|---|---|---|---|
| Symptoms/Criteria | | males | females |
| Clinical signs | | none | none |
| mortality | within 6 h | 0 | 0 |
| | within 24 h | 0 | 0 |
| | within 7 d | 0 | 0 |
| | within 14 d | 0 | 0 |
| Mean body weight | start | 18.2 | 17.6 |
| | after 7 d | 19.8<br>(+8.8) | 18.4<br>(+29.2) |
| | after 14 d | 22.4<br>(+23.1) | 20.6<br>(+37.8) |
| Inhibition of body weight gain | | none | none |
| Necropsy findings | | none | none |

D = days
H = hours
In brackets: body weight gain in %, compared with the start value
i.v. = intravenous In-vitro analysis with human cells: The treatment is only administered once to patients and is being administered by the tolerogenic i.v. route with cells undergoing apoptosis. Thus there is little concern that a cytotoxic/anaphylactic response will be induced following administration of cells. A possible reaction between treated cells and T cells from recipient patient in-vitro can be tested by a mixed lymphocyte reaction prior to the study in healthy donors and MS patients. These assays document proliferation as well as cytokine release.

Proliferation assays against the antigen used in the trial will generate short term TCL. These antigen-specific T cells are co-cultured with autologous ECDI fixed antigen coupled APC in a 24 well culture plate at 37° C. in 5% $CO_2$ at a ratio of 1:1 to 1:2 (T:APC) with total $2-4 \times 10^6$ total mixed cells. After 24 h cultured cell mixtures are collected and applied to a Ficoll gradient to isolate viable cells. After washing in culture medium (RPMI 1640) live cells are remixed with antigen in the presence of APC and evaluated for proliferation, activation status by FACS, cytokine secretion (IL-2, IL-4, IFN-g, IL-17) and cytokine mRNA expression. Depending on the timing of restimulation, one might expect anergy induction and/or induction of activation-induced cell death (AICD). Such cases should be properly documented.

The objective of this study was to evaluate the effect of peptide-coupled PBMC on immune activation of PBMC in-vitro. PBMC from MS patients (n=2) and a healthy control were cultured in the presence of peptide-coupled PBMC and analysed for proliferation response by thymidine incorporation and cytokine secretion (IL12, IFN-γ, IL10, IL1β, TNF-α) using a FACS based array (FlowCytomix, Bendermedsystems).

To assess cell proliferation in response to peptide-coupled cells, PBMC were seeded in two 96 well plates at $1\times10^5$ cells/well in complete IMDM containing 100 U/ml penicillin/streptomycin, 50 µg/ml gentamicin, 2 mM L-gutamine, 5% heat decomplemented human serum. To the respective wells, either $5\times10^4$ PBMC treated with EDC in the presence of the 7 peptides used in the trial (=peptide-coupled PBMC, tAPCpep), $5\times10^4$ PBMC treated with EDC but without peptide (tAPC), 2.5 µg/ml phytohhaemagglutinin (PHA) or without further stimulus (APC) were added.

Figure 3:
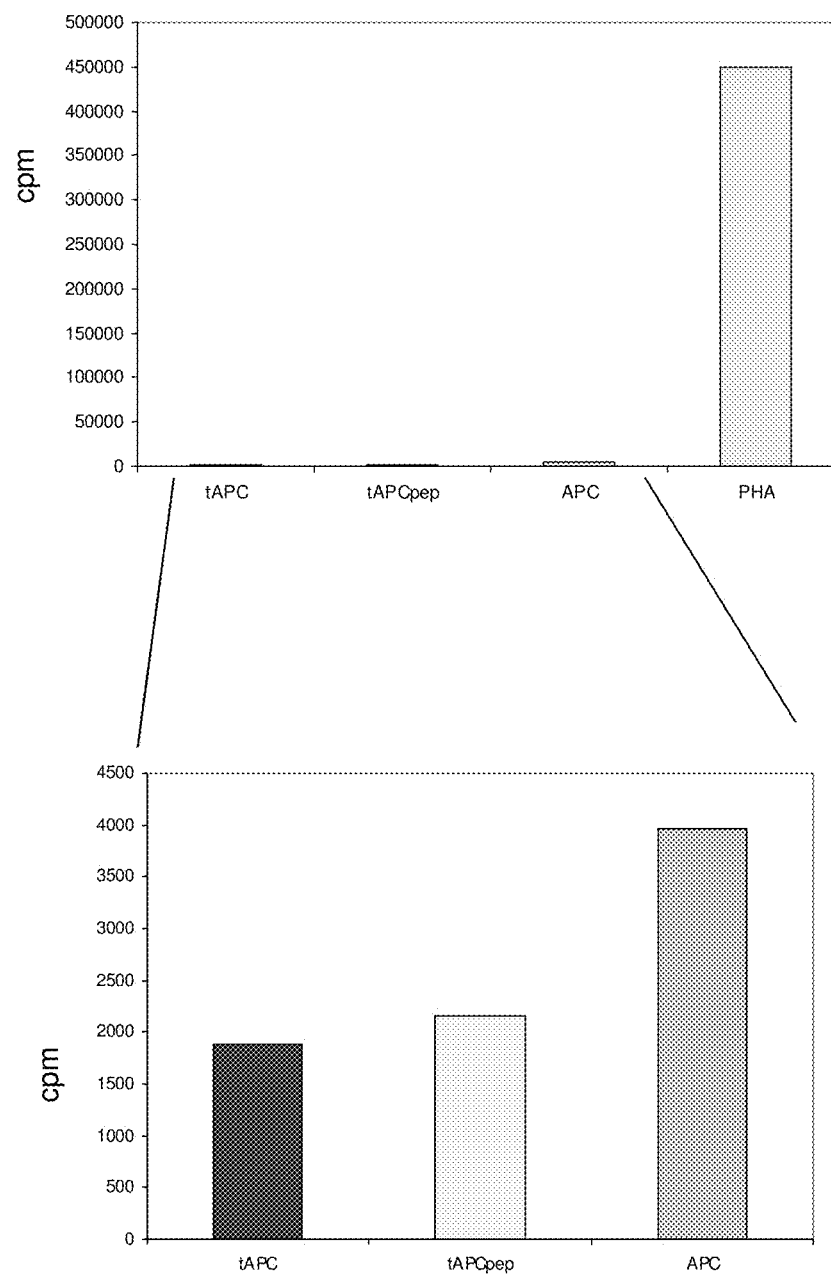
FIG. 3 shows that presence of peptide-coupled cells did not induce proliferation in PBMC compared to unstimulated PBMC or PHA stimulated PBMC. The inset shows counts with PBMC treated with EDC but without peptide (tAPC), prep (tAPCprep) or without further stimulus (APC).

Presence of peptide-coupled cells did not induce proliferation in PBMC compared to unstimulated PBMC or PHA stimulated PBMC (FIG. 3).

The presence of inflammatory cytokines after 3 h and 24 h was also analyzed. Briefly, PBMC were cultured overnight in complete IMDM containing 100 U/ml penicillin/streptomycin, 50 µg/ml gentamicin, 2 mM L-gutamine, 5% heat decomplemented human serum, either in the presence of 2.5 µg/ml PHA or without stimulus. After 24 h, cells were washed in complete IMDM and seeded in a 24 well plate ($4\times10^6$/ml) in the presence of either PBMC treated with EDC and 7 peptides used in the trial (=peptide-coupled PBMC, tAPCpep), $1\times10^6$ PBMC treated with EDC but without peptide (tAPC), 2.5 µg/ml PHA (PHA) or without further stimulus (APC).

Figure 4:
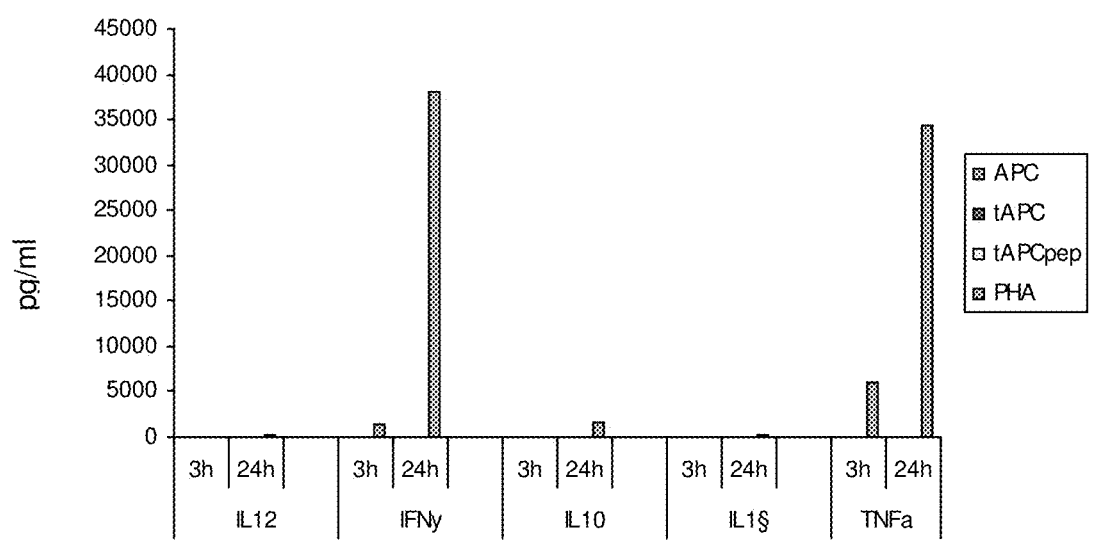
FIG. 4 shows that there is no significant induction of various inflammatory cytokines (e.g., IL10, IFNγ, IL10, IL1§, TNFα) at 3 hr and 24 hr in the presence of peptide-coupled PBMC compared to the negative control (APC).
Figure 5:
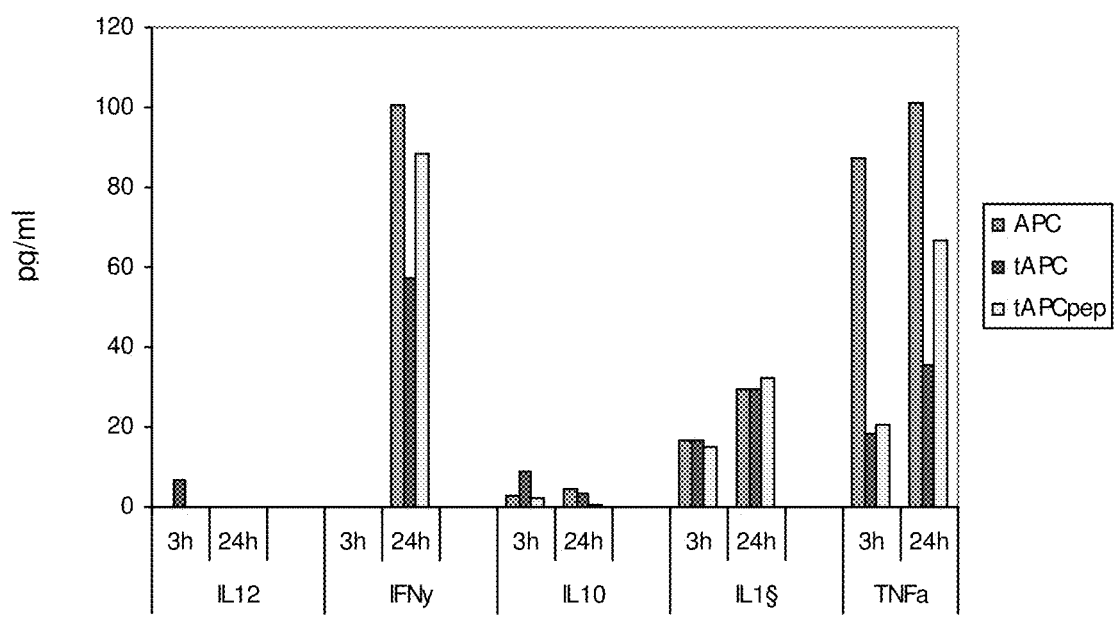
FIG. 5 shows the concentrations of cytokines (at 3 hr and 24 hr) without PHA control.

As depicted in FIG. 4 and FIG. 5 there is no significant induction of inflammatory cytokines in the presence of peptide-coupled PBMC compared to the negative control (APC).

Depicted in FIG. 5 are the concentrations of cytokines without PHA control.

Figure 6:
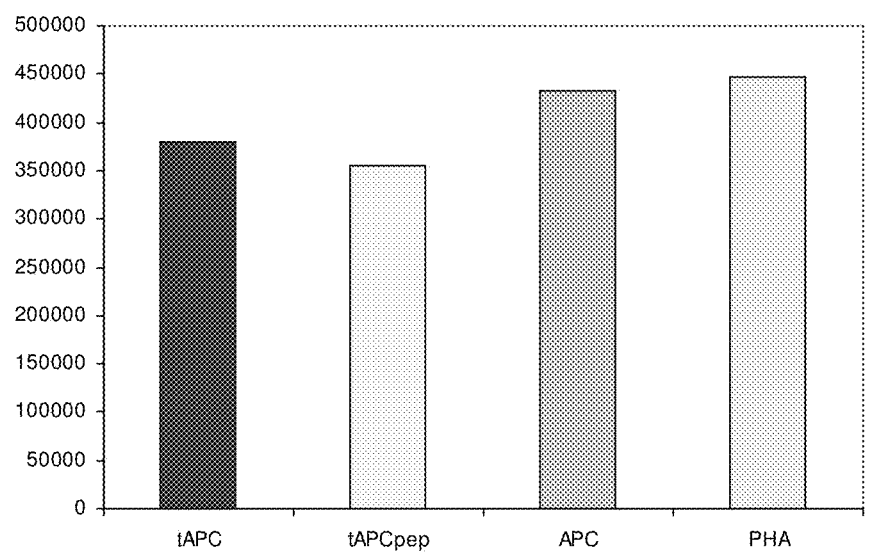
FIG. 6 shows cytokine response in PBMC pre-activated with PHA and cultured in the presence of APC, tAPC or tAPCpep. It can be seen that there was no induction of proliferation in response to peptide-coupled cells.
Figure 7:
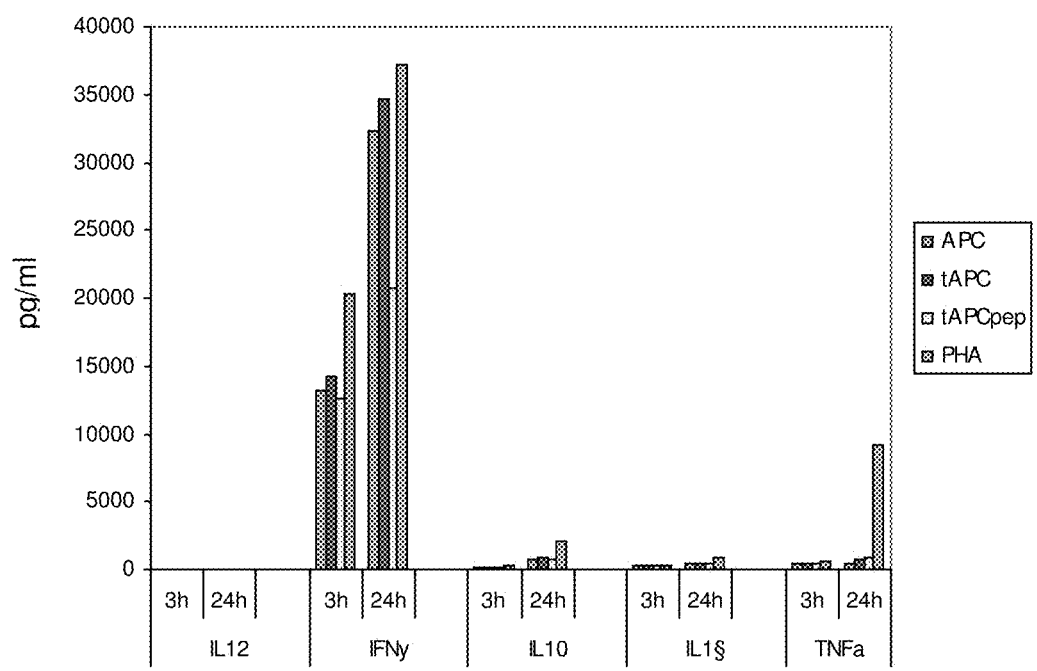
FIG. 7 shows a plot of cytokine release (at 3 hr and 24 hr) in response to peptide-coupled cells.

To analyze whether the response to peptide coupled cells differs dependent on the activation status of the cells, PBMC were pre-activated with PHA for 24 h and added the peptide-coupled PBMC. There was no induction of proliferation (FIG. 6) or cytokines (FIG. 7) in response to peptide-coupled cells.

In summary, the presence of peptide-coupled cells in-vitro did not induce activation of immune cells. These results correlate well with the results on the tolerization of human T-cell clones in-vitro and the induction of tolerance with peptide-coupled cells in-vivo in different animal models (34).

Potency of Human Peptide Coupled Cells in-vitro

Figure 8:
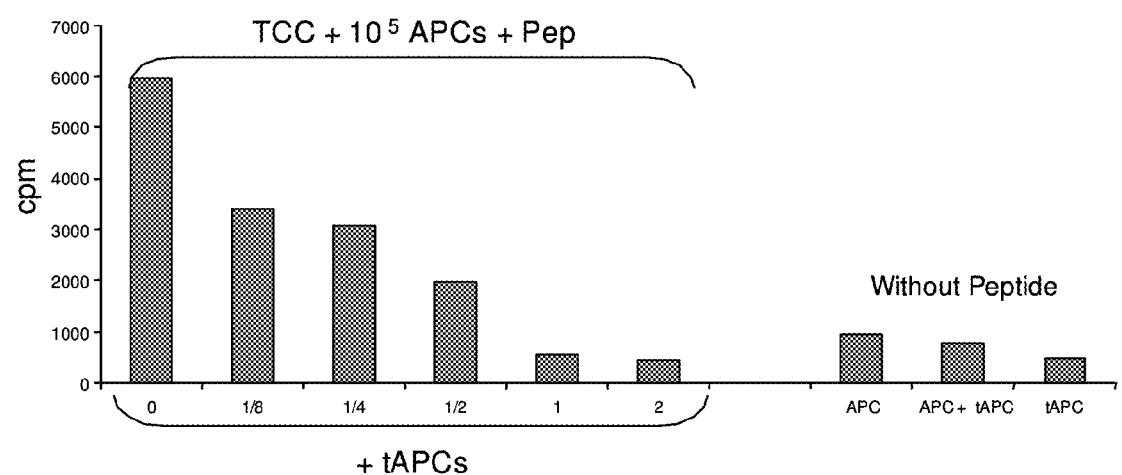
FIG. 8 shows proliferative response of the TCC, as measured by $^3$H-Thymidine incorporation after 72 h.

The objective of the study was to evaluate the effect of peptide-coupled cells on the antigen-specific response of human T cells. A T-cell clone (TCC) obtained from the cerebrospinal fluid (CSF) of an MS patient during relapse was used. Briefly, TCC ($2\times10^4$ cells/well) was cultured in complete IMDM (containing 100 U/ml penicillin/streptomycin, 50 µg/ml gentamicin, 2 mM L-gutamine, 5% heat decomplemented human serum) and pulsed with the peptide (MSI118) in the presence of irradiated PBMC ($1\times10^5$ cells/well). Peptide (MSI118, 10 µg/ml) coupled PBMC were added to the wells at different cell concentrations. Proliferative response of the TCC was measured by $^3$H-Thymidine incorporation after 72 h (FIG. 8).

Incubation of TCC with the specific peptide in the presence of antigen-coupled cells reduces the antigen specific response measured by thymidine incorporation in a dose-dependent manner.

Figure 9:
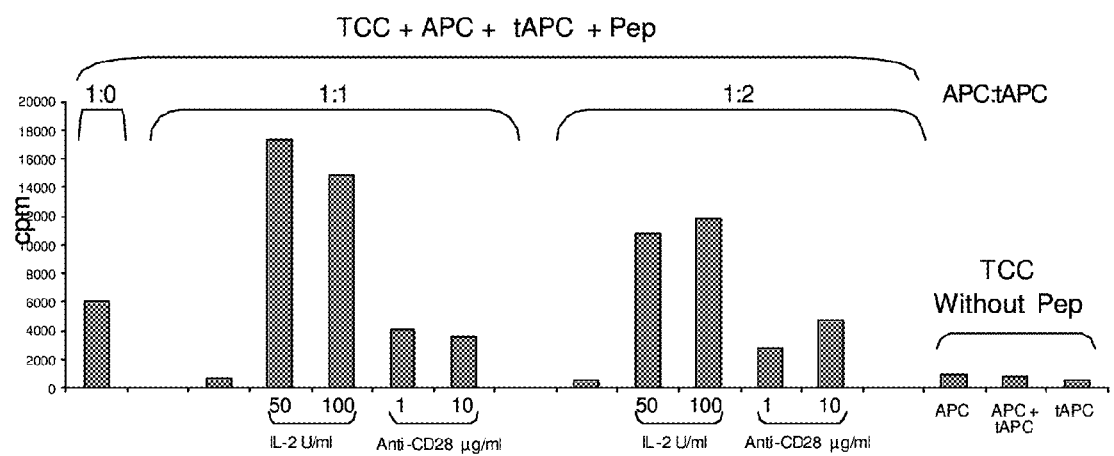
FIG. 9 shows that proliferation of the TCC can be recuperated by the addition of either IL-2 or the anti-CD28 antibody in the presence of peptide-coupled cells.

To exclude a toxic inhibition of the peptide-coupled cells on the TCC, IL-2 or anti-CD28 monoclonal antibody were added to respective wells. As depicted in FIG. 9, proliferation of the TCC can be recuperated by the addition of either IL-2 or the anti-CD28 antibody in the presence of peptide-coupled cells.

It has been suggested that by fixing peptide pulsed antigen presenting cells a immunologic synapse cannot be formed and anergy is induced in autoreactive T-cells through presentation of the peptide through the MHC without co-stimulation. The immunologic synapse refers to the spatially organized motif of membrane proteins and cytosolic molecules that forms at the junction between T cell and an antigen presenting cell.

To further explore the invention, the formation of the immunologic synapse is analyzed by fluorescence microscopy and by analyzing the biophysical parameters (e.g. calcium influx) characterizing TCR MHC interaction.

Until now it is not clear from the literature, neither from the animal model, nor human studies, which subset of antigen presenting cells is most important in the tolerization process. This question was examined by analyzing the potency of the regimen as described above, after isolating specific cells from the PBMC population. Isolation of cells is performed using columns with labelled beads or a cell sorter.

Comparable results may be achieved on the basis of red blood cells (erythrocytes) chemically coupled with one of the cocktails of peptides defined herein. It is clear that in case of red blood cells the step of erythrocyte lysis has to be avoided and that cell-collection procedures have to be adapted accordingly.

Definition Of Myelin Peptides

The myelin peptides specifically disclosed in this application are characterized by the following sequences:

$MBP_{13-32}$ (SEQ ID NO: 1):
KYLATASTMDHARHGFLPRH $MBP_{83-99}$ (SEQ ID NO: 2):
ENPVVHFFKNIVTPRTP $MBP_{111-129}$ (SEQ ID NO: 3):
LSRFSWGAEGQRPGFGYGG $MBP_{146-170}$ (SEQ ID NO: 4):
AQGTLSKIFKLGGRDSRSGSPMARR $PLP_{139-154}$ (SEQ ID NO: 5):
HCLGKWLGHPDKFVGI $MOG_{1-20}$ (SEQ ID NO: 6):
GQFRVIGPRHPIRALVGDEV $MOG_{35-55}$ (SEQ ID NO: 7):
MEVGWYRPPFSRVVHLYRNGK $MBP_{82-98}$ (SEQ ID NO: 8):
DENPVVHFFKNIVTPRT $MBP_{82-99}$ (SEQ ID NO: 9):
DENPVVHFFKNIVTPRTP $MBP_{82-106}$ (SEQ ID NO: 10):
DENPVVHFFKNIVTPRTPPPSQGKG $MBP_{87-106}$ (SEQ ID NO: 11):
VHFFKNIVTPRTPPPSQGKG $MBP_{131-155}$ (SEQ ID NO: 12):
ASDYKSAHKGLKGVDAQGTLSKIFK $PLP_{41-58}$ (SEQ ID NO: 13):
GTEKLIETYFSKNYQDYE $PLP_{89-106}$ (SEQ ID NO: 14):
GFYTTGAVRQIFGDYKTT

PLP₉₅₋₁₁₆ (SEQ ID NO: 15):
AVRQIFGDYKTTICGKGLSATV

PLP₁₇₈₋₁₉₇ (SEQ ID NO: 16):
NTWTTCQSIAFPSKTSASIG

PLP₁₉₀₋₂₀₉ (SEQ ID NO: 17):
SKTSASIGSLCADARMYGVL

MOG₁₁₋₃₀ (SEQ ID NO: 18):
PIRALVGDEVELPCRISPGK

MOG₂₁₋₄₀ (SEQ ID NO: 19):
ELPCRISPGKNATGMEVGWY

MOG₆₄₋₈₆ (SEQ ID NO: 20):
EYRGRTELLKDAIGEGKVTLRIR

PLP (human) full length protein
SEQ ID NO: 21
MGLLECCARCLVGAPFASLV ATGLCFFGVALFCGCGHEALTGTEKLIET

YFSKNYQDYEYLINVIHAFQVVIYGTASFFFLYGALLLAEGFYTTGAVRQ

IFGDYKTTICGKGLSATVTGGQKGRGSRGQHQAHSLERVCHCLGKWLGHP

DKITYALTVVWLLVFACSAVPVYIYFNTWTTCQSIAFPSKTSASIGSLCA

DARMYGVLPWNAFPGKVCGSNLLSICKTAEFQMTFHLFIAAFVGAAATLV

SLLTFMIAATYNFAVLKLMGRGTKF

MBP (human) full length protein (18.5Kd isoform)
SEQ ID NO: 22
ASQKRPSQRHGSKYLATASTMDHARHGFLPRHRDTGILDSLGRFFGGDRG

APKRGSGKDSHHAARTTHYGSLPQKSHGRTQDENPVVHFF

KNIVTPRTPPPSQGKGRGLSLSRFSWGAEGQRPGFGYGGRASDYKSAHKG

LKGVDAQGTLSKIFKLGGRD SRSGSPMARR

MOG (human) full length protein
SEQ ID NO: 23
MASLSRPSLPSCLCSFLLLLLLQVSSSYAGQFRVIGPRHPIRALVGDEVE

LPCRISPGKNATGMEVGWYRPPFSRVVHLYRNGKDQDGDQAPEYRGRTEL

LKDAIGEGKVTLRIRNVRFSDEGGFTCFFRDHSYQEEAAMELKVEDPFYW

VSPGVLVLLAVLPVLLLQITVGLVFLCLQYRLRGKLRAEIENLHRTFDPH

FLRVPCWKITLFVIVPVLGPLVALIICYNWLHRRLAGQFLEELRNPF

Specific Citrullinated Sequences (See Lit. ref. 46, below):
MBP₁₈₋₃₈ (Cit) (SEQ ID NO: 24):
ASTMDHACitHGFLPCitHRDTGIL MBP₁₁₅₋₁₃₁ (Cit) (SEQ ID NO: 25):
SWGAEGQCitPGFGYGGCitA MBP₁₅₁₋₁₇₀ (Cit) (SEQ ID NO: 26):
SKIFKLGGCitDSRSGSPMARR The sequences defined above include different end modifications of the peptides, e.g. acetylation, amidation, carboxylation.

EXAMPLE 1.5-2×10⁹ peripheral blood mononuclear cells are isolated from a MS patient. The isolated cells are coupled according to the manufacture process described above with a cocktail of the following peptides MBP₁₃₋₃₂, MBP₈₃₋₉₉, MBP₁₁₁₋₁₂₉, MBP₁₄₆₋₁₇₀, PLP₁₃₉₋₁₅₄, MOG₁₋₂₀ and MOG₃₅₋₅₅. The resulting suspension of approximately 10⁹ cells suspended in 100 ml water buffered to pH 7.2-7.8 is infused intravenously to the patient. MRI examinations carried out before and after application (e.g. 1 day, 1 week, 1 month, 6 months, 1 year after application) convincingly demonstrates the efficacy of the procedure in terms of reduction of CNS-inflammation. The MRI findings are in line with other clinical symptoms.

It will be appreciated by the expert skilled in the art that the description relating to the manufacturing process (including all tests and validation steps) are provided as examples. They are not meant to limit the invention in any way. The expert skilled in the art will certainly be able to carry out the invention as described above but also to modify the invention in various aspects based on his general knowledge without any need to be inventive.

LITERATURE REFERENCES

1. Miller, S. D., D. M. Turley, and J. R. Podojil. 2007. Antigen-specific tolerance strategies for the prevention and treatment of autoimmune disease. *Nat Rev Immunol* 7:665.
2. Bielekova, B., M. H. Sung, N. Kadom, R. Simon, H. McFarland, and R. Martin. 2004. Expansion and functional relevance of high-avidity myelinspecific CD4+ T cells in multiple sclerosis. *J Immunol* 172:3893.
3. Pope, L., P. Y. Paterson, and S. D. Miller. 1992. Antigen-specific inhibition of the adoptive transfer of experimental autoimmune encephalomyelitis in Lewis rats. *J Neuroimmunol* 37:177.
4. Bielekova, B., B. Goodwin, N. Richert, I. Cortese, T. Kondo, G. Afshar, B. Gran, J. Eaton, J. Antel, J. A. Frank, H. F. McFarland, and R. Martin. 2000. Encephalitogenic potential of the myelin basic protein peptide (amino acids₈₃₋₉₉) in multiple sclerosis: results of a phase II clinical trial with an alteredpeptide ligand. *Nat Med* 6:1167
5. Krogsgaard, M., K. W. Wucherpfennig, B. Cannella, B. E. Hansen, A. Svejgaard, J. Pyrdol, H. Ditzel, C. Raine, J. Engberg, and L. Fugger. 2000. Visualization of myelin basic protein (MBP) T cell epitopes in multiple sclerosis lesions using a monoclonal antibody specific for the human histocompatibility leukocyte antigen (HLA)-DR2-MBP 85-99 complex. *J Exp Med* 191:1395.
6. Warren, K. G., I. Catz, L. Z. Ferenczi, and M. J. Krantz. 2006. Intravenous synthetic peptide MBP₈₂₋₉₈ delayed disease progression in an HLA Class II defined cohort of patients with progressive multiple sclerosis: results of a 24-month double-blind placebo-controlled clinical trial and 5 years of follow-uptreatment. *Eur J Neurol* 13:887.
7. Warren, K. G., I. Catz, and K. W. Wucherpfennig. 1997. Tolerance induction to myelin basic protein by intravenous synthetic peptides containing epitope P85 VVH-FFKNIVTP96 in chronic progressive multiple sclerosis. *J Neurol Sci* 152:31.
8. Beuvery, E. C., G. J. Speijers, B. I. Lutz, D. Freudenthal, V. Kanhai, B. Haagmans, and H. J. Derks. 1986. Analytical, toxicological and immunological consequences of the use of N-ethyl-N'-(3-dimethylaminopropyl) carbodiimide as coupling reagent for the preparation of meningococcal group C polysaccharide-tetanus toxoid conjugate as vaccine or human use. *Dev Biol Stand* 63:117
9. Drager, L. J., U. Julius, K. Kraenzle, J. Schaper, M. Toepfer, K. Zygan, V. Otto, and E. Steinhagen-Thiessen. 1998. DALI—the first human whole-blood low-density lipoprotein and lipoprotein (a) apheresis system in clinical use: procedure and clinical results. *Eur J Clin Invest* 28:994.
10. Liu, Y., L. Gan, D. J. Carlsson, P. Fagerholm, N. Lagali, M. A. Watsky, R. Munger, W. G. Hodge, D. Priest, and M.

Griffith. 2006. A simple, crosslinked collagen tissue substitute for corneal implantation. *Invest Ophthalmol Vis Sci* 47:1869.

11. Moshnikova, A. B., V. N. Afanasyev, O. V. Proussakova, S. Chemyshov, V. Gogvadze, and I. P. Beletsky. 2006. Cytotoxic activity of 1-ethyl-3-(3-dimethylaminopropyl)-carbodiimide is underlain by DNA interchain crosslinking. *Cell Mol Life Sci* 63:229.

12. Schneerson, R., O. Barrera, A. Sutton, and J. B. Robbins. 1980. aration, characterization, and immunogenicity of *Haemophilus influenzae* type b polysaccharide-protein conjugates. *J Exp Med* 152:361.

13. Tai, J. Y., P. P. Vella, A. A. McLean, A. F. Woodhour, W. J. McAleer, A. Sha, C. Dennis-Sykes, and M. R. Hilleman. 1987. *Haemophilus influenzae* type b polysaccharide-protein conjugate vaccine. *Proc Soc Exp Biol Med* 184:154.

14. Wilchek, M., T. Miron, and J. Kohn. 1981. A highly sensitive colorimetric method for the determination of carbodiimides. *Anal Biochem* 114:419.

15. Miller, S. D., R. P. Wetzig, and H. N. Claman. 1979. The induction of cellmediated immunity and tolerance with protein antigens coupled to syngeneic lymphoid cells. *J Exp Med* 149:758.

16. Kennedy, M. K., M. C. Dal Canto, J. L. Trotter, and S. D. Miller. 1988. Specific immune regulation of chronic-relapsing experimental allergic encephalomyelitis in mice. *J Immunol* 141:2986.

17. Tan, L. J., M. K. Kennedy, M. C. Dal Canto, and S. D. Miller. 1991. Successful treatment of paralytic relapses in adoptive experimental autoimmune encephalomyelitis via neuroantigen-specific tolerance. *J Immunol* 147:1797.

18. Vandenbark, A. A., M. Vainiene, K. Ariail, S. D. Miller, and H. Offner. 1996. Prevention and treatment of relapsing autoimmune encephalomyelitis with myelin peptide-coupled splenocytes. *J Neurosci Res* 45:430.

19. Karpus, W. J., J. G. Pope, J. D. Peterson, M. C. Dal Canto, and S. D. Miller. 1995. Inhibition of Theiler's virus-mediated demyelination by peripheral immune tolerance induction. *J Immunol* 155:947.

20. Miller, S. D., B. L. McRae, C. L. Vanderlugt, K. M. Nikcevich, J. G. Pope, L. Pope, and W. J. Karpus. 1995. Evolution of the T-cell repertoire during the course of experimental immune-mediated demyelinating diseases. *Immunol Rev* 144:225.

21. Jenkins, M. K., and R. H. Schwartz. 1987. Antigen presentation by chemically modified splenocytes induces antigen-specific T cell unresponsiveness in vitro and in vivo. *J Exp Med* 165:302.

22. Turley, D. M., and S. D. Miller. 2007. Peripheral tolerance induction using ethylenecarbodiimide-fixed APCs uses both direct and indirect mechanisms of antigen presentation for prevention of experimental autoimmune encephalomyelitis. *J Immunol* 178:2212.

23. Kennedy, M. K., L. J. Tan, M. C. Dal Canto, V. K. Tuohy, Z. J. Lu, J. L. Trotter, and S. D. Miller. 1990. Inhibition of murine relapsing experimental autoimmune encephalomyelitis by immune tolerance to proteolipid protein and its encephalitogenic peptides. *J Immunol* 144:909.

24. Tan, L. J., M. K. Kennedy, and S. D. Miller. 1992. Regulation of the effector stages of experimental autoimmune encephalomyelitis via neuroantigenspecific tolerance induction. II. Fine specificity of effector T cell inhibition. *J Immunol* 148:2748.

25. Vanderlugt, C. L., K. L. Neville, K. M. Nikcevich, T. N. Eagar, J. A. Bluestone, and S. D. Miller. 2000. Pathologic role and temporal appearance of newly emerging autoepitopes in relapsing experimental autoimmune encephalomyelitis. *J Immunol* 164:670.

26. Karpus, W. J., N. W. Lukacs, B. L. McRae, R. M. Strieter, S. L. Kunkel, and S. D. Miller. 1995. An important role for the chemokine macrophage inflammatory protein-1 alpha in the pathogenesis of the T cell-mediated autoimmune disease, experimental autoimmune encephalomyelitis. *J Immunol* 155:5003.

27. Kennedy, M. K., L. J. Tan, M. C. Dal Canto, and S. D. Miller. 1990. Regulation of the effector stages of experimental autoimmune encephalomyelitis via neuroantigen-specific tolerance induction. *J Immunol* 145:117

28. Miller, S. D., L. J. Tan, M. K. Kennedy, and M. C. Dal Canto. 1991. Specific immunoregulation of the induction and effector stages of relapsing EAE via neuroantigen-specific tolerance induction. *Ann N Y Acad Sci* 636:79.

29. Smith, C. E., T. N. Eagar, J. L. Strominger, and S. D. Miller. 2005. Differential induction of IgE-mediated anaphylaxis after soluble vs. cellbound tolerogenic peptide therapy of autoimmune encephalomyelitis. *Proc Natl Acad Sci USA* 102:9595.

30. Braley-Mullen, H., J. G. Tompson, G. C. Sharp, and M. Kyriakos. 1980. Suppression of experimental autoimmune thyroiditis in guinea pigs by pre-treatment with thyroglobulin-coupled spleen cells. *Cell Immunol* 51:408.

31. Gregorian, S. K., L. Clark, E. Heber-Katz, E. P. Amento, and A. Rostami. 1993. Induction of peripheral tolerance with peptide-specific anergy in experimental autoimmune neuritis. *Cell Immunol* 150:298.

32. Dua, H. S., D. S. Gregerson, and L. A. Donoso. 1992. Inhibition of experimental autoimmune uveitis by retinal photoreceptor antigens coupled to spleen cells. *Cell Immunol* 139:292.

33. Kennedy, K. J., W. S. Smith, S. D. Miller, and W. J. Karpus. 1997. Induction of antigen-specific tolerance for the treatment of ongoing, relapsing autoimmune encephalomyelitis: a comparison between oral and peripheral tolerance. *J Immunol* 159:1036.

34. Vandenbark, A. A., D. Barnes, T. Finn, D. N. Bourdette, R. Whitham, I. Robey, J. Kaleeba, B. F. Bebo, Jr., S. D. Miller, H. Offner, and Y. K. Chou. 2000. Differential susceptibility of human T(h)1 versus T(h) 2 cells to induction of anergy and apoptosis by ECDI/antigen-coupled antigenpresenting cells. *Int Immunol* 12:57.

35. Bielekova, B., A. Lincoln, H. McFarland, and R. Martin. 2000. Therapeutic potential of phosphodiesterase-4 and -3 inhibitors in Th1-mediated autoimmune diseases. *J Immunol* 164:1117.

36. Bielekova, B., N. Richert, T. Howard, G. Blevins, S. Markovic-Plese, J. McCartin, J. A. Frank, J. Wurfel, J. Ohayon, T. A. Waldmann, H. F. McFarland, and R. Martin. 2004. Humanized anti-CD25 (daclizumab) inhibits disease activity in multiple sclerosis patients failing to respond to interferon beta. *Proc Natl Acad Sci USA* 101:8705.

37. Calabresi, P. A., N. S. Fields, H. W. Maloni, A. Hanham, J. Carlino, J. Moore, M. C. Levin, S. Dhib-Jalbut, L. R. Tranquill, H. Austin, H. F. McFarland, and M. K. Racke. 1998. Phase 1 trial of transforming growth factor beta 2 in chronic progressive MS. *Neurology* 51:289.

38. Frank, J. A., N. Richert, B. Lewis, C. Bash, T. Howard, R. Civil, R. Stone, J. Eaton, H. McFarland, and T. Leist. 2002. A pilot study of recombinant insulin-like growth factor-1 in seven multiple sderosis patients. *Mult Scler* 8:24.

39. Paty, D. W., and D. K. Li. 1993. Interferon beta-1b is effective in relapsingremitting multiple sclerosis. II. MRI analysis results of a multicenter, randomized, double-blind, placebo-controlled trial. UBC MS/MRI Study Group and the IFNB Multiple Sclerosis Study Group. *Neurology* 43:662.
40. Filippi, M., M. A. Horsfield, H. J. Ader, F. Barkhof, P. Bruzzi, A. Evans, J. A. Frank, R. I. Grossman, H. F. McFarland, P. Molyneux, D. W. Paty, J. Simon, P. S. Tofts, J. S. Wolinsky, and D. H. Miller. 1998. Guidelines for using quantitative measures of brain magnetic resonance imaging abnormalities in monitoring the treatment of multiple sclerosis. *Ann Neurol* 43:499.
41. McFarland, H. F., J. A. Frank, P. S. Albert, M. E. Smith, R. Martin, J. O. Harris, N. Patronas, H. Maloni, and D. E. McFarlin. 1992. Using gadoliniumenhanced magnetic resonance imaging lesions to monitor disease activity in multiple sclerosis. *Ann Neurol* 32:758.
42. Miller, D. H., F. Barkhof, and J. J. Nauta. 1993. Gadolinium enhancement increases the sensitivity of MRI in detecting disease activity in multiple sclerosis. *Brain* 116 (Pt 5):1077.
43. Miller, S. D., Smith, C. E. 2006. Multi-peptide coupled-cell tolerance ameliorates ongoing relapsing EAE associated with multiple pathogenic autoreactivities. *J Autoimmunity* 27:218.
44. Kohm, A. P., Turley, D. M., Miller, S. D., 2005. Targeting the TCR: T-Cell Receptor and Peptide-Specific Tolerance-Based Strategies for Restoring Self-Tolerance in CNS Autoimmune Disease. *Int Rev Immunol* 24:361.
45. Moscarello et al., 2006. The Role of Citrullinated Protein Suggests a Novel Mechanism in the Pathogenesis of Multiple Sclerosis. Neurochem Res 32:251-256.
46. Tranquill et al. 2000. Enhanced T cell responsiveness to citrulline-containing myelin basic protein in multiple sclerosis patients 6:220-225
47. Kamholz et al. 1986. Identification of three forms of human myelin basic protein by cDNA cloning. Proc Natl Acad Sci USA. 83:4962-4966.
48. Lutterotti A, Yousef S, Sputtek A, Stürner K, Stellmann J, Breiden P, Reinhardt S, Schulze C, Bester M, Heesen C, Schippling S et al: Antigen-specific tolerance by autologous myelin peptide-coupled cells—a phase i trial in multiple sclerosis. *Science Translational Medicine* (2013), June 5;5(188):188ra75.doi:10.1126/scitranslmed.3006168.

All of the references cited above are incorporated herein by reference.

The invention claimed is:

1. A chemically coupled cell which is a peripheral blood mononuclear cell (PBMC) or a red blood cell erythrocyte that is chemically coupled to at least six peptides selected from the group consisting of: $MBP_{13-32}$ (SEQ ID NO:1), $MBP_{83-99}$ (SEQ ID NO:2), $MBP_{111-129}$ (SEQ ID NO:3), $MBP_{82-98}$ (SEQ ID NO:8), $MBP_{82-99}$ (SEQ ID NO:9), $MBP_{82-106}$ (SEQ ID NO:10), $MBP_{87-106}$ (SEQ ID NO:11), $MBP_{131-155}$ (SEQ ID NO:12), $MBP_{146-170}$ (SEQ ID NO:4), $PLP_{41-58}$ (SEQ ID NO:13), $PLP_{89-106}$ (SEQ ID NO:14), $PLP_{95-116}$ (SEQ ID NO:15), HCLGKWLGHPDKFVGI (SEQ ID NO:5), $PLP_{178-197}$ (SEQ ID NO:16), SKTSASIGSLCADARMYGVL (SEQ ID NO:17), $MOG_{1-20}$ (SEQ ID NO:6), $MOG_{11-30}$ (SEQ ID NO:18), $MOG_{21-40}$ (SEQ ID NO:19), $MOG_{35-55}$ (SEQ ID NO:7), and $MOG_{64-86}$ (SEQ ID NO:20), wherein MBP is myelin basic protein, PLP is proteolipid protein and MOG is myelin oligodendrocyte protein.

2. The chemically coupled cell according to claim 1, which cell is a red blood cell (RBC).

3. The chemically coupled cell according to claim 1, which cell is a peripheral blood mononuclear cell (PBMC).

4. The chemically coupled cell according to claim 1, wherein the peptides are chemically coupled by 1-ethyl-3-(3-dimethylaminopropyl)-carbodiimide (ECDI).

5. A pharmaceutical composition comprising the chemically coupled cell according to claim 1 and a pharmaceutically acceptable excipient.

6. A medical product comprising one or more of the chemically coupled cells according to claim 1 and an anti-coagulant.

7. A chemically coupled cell which is a peripheral blood mononuclear cell (PBMC) or a red blood cell (RBC) that is chemically coupled to each peptide in a cocktail of peptides selected from the group consisting of cocktails e-h, j-kk, mm, and nn of tables 5.1-5.3.

8. The chemically coupled cell according to claim 7, wherein one of the MBP peptides is a citrullinated MBP peptide.

9. A chemically coupled cell which is a peripheral blood mononuclear cell (PBMC) or a red blood cell (RBC) that is chemically coupled to each peptide in a cocktail of peptides selected from the group consisting of cocktails e-h, j-kk, mm, and nn of tables 5.1-5.3 with the proviso that at least one of the myelin basic protein (MBP) peptides has been replaced with the full-length MBP protein.

10. The chemically coupled cell according to claim 9, wherein the full length MBP protein is the 18.5 kD isoform according to SEQ ID NO: 22.

11. A chemically coupled cell which is a peripheral blood mononuclear cell (PBMC) or a red blood cell (RBC) that is chemically coupled to each peptide in a cocktail of peptides selected from the group consisting of cocktails e-h, j-kk, mm, and nn with the proviso that at least one of the proteolipid protein (PLP) peptides has been replaced with the full-length PLP protein of SEQ ID NO: 21.

12. A chemically coupled cell which is a peripheral blood mononuclear cell (PBMC) or a red blood cell (RBC) that is chemically coupled to each peptide in a cocktail of peptides selected from the group consisting of cocktails e-h, j-kk, mm, and nn with the proviso that at least one of the myelin oligodendrocyte glycoprotein (MOG) peptides has been replaced with the full-length MOG protein according to SEQ ID NO: 23.

13. A method for the treatment of an autoimmune inflammatory disease in a subject in need thereof, comprising administering into said subject a therapeutically effective amount of said chemically coupled cells according to claim 1.

14. The method according to claim 13, wherein the autoimmune inflammatory disease is multiple sclerosis (MS).

15. The method according to claim 13, wherein the chemically coupled cells are allogenic cells relative to said subject.

16. The method according to claim 13, wherein the chemically coupled cells are autologous cells relative to said subject.

17. A process for the manufacture of a chemically coupled cell according to claim 1, comprising
 (a) contacting in the presence of a coupling agent (i) a peripheral blood mononuclear cell (PBMC) or a red blood cell (RBC) with (ii) at least six peptides selected from the group consisting of: $MBP_{13-32}$ (SEQ ID NO:1), $MBP_{83-99}$ (SEQ ID NO:2), $MBP_{111-129}$ (SEQ ID NO:3), $MBP_{82-98}$ (SEQ ID NO:8), $MBP_{82-99}$ (SEQ ID NO:9), $MBP_{82-106}$ (SEQ ID NO:10), $MBP_{87-106}$ (SEQ ID NO:11), $MBP_{131-155}$ (SEQ ID NO:12), $MBP_{146-170}$ (SEQ ID NO:4), $PLP_{41-58}$ (SEQ ID NO:13), $PLP_{89-106}$ (SEQ ID NO:14), $PLP_{95-116}$ (SEQ ID NO:15), HCLGKWLGHPDKFVGI (SEQ ID NO:5), $PLP_{178-197}$ (SEQ ID NO:16), SKTSASIGSLCADARMYGVL (SEQ ID NO:17), $MOG_{1-20}$ (SEQ ID NO:6), $MOG_{11-30}$ (SEQ ID NO:18), $MOG_{21-40}$ (SEQ ID NO:19), $MOG_{35-55}$ (SEQ ID NO:7), and $MOG_{64-86}$ (SEQ ID NO:20), wherein MBP is myelin basic protein, PLP is proteolipid protein and MOG is myelin oligodendrocyte protein and
 (b) carrying out a chemical reaction to couple the cell to each of the at least six peptides, thereby forming said chemically coupled cell.

18. The process according to claim 17, wherein the coupling agent is 1-ethyl-3-(3-dimethylaminopropyl)-carbodiimide (ECDI).

19. A process for the manufacture of a chemically coupled cell according to claim 7, comprising
 (a) contacting in the presence of a coupling agent (i) a peripheral blood mononuclear cell (PBMC) or a red blood cell (RBC) with (ii) at least one of said cocktail of peptides e-h, j-kk, mm, or nn of tables 5.1-5.3, and
 (b) carrying out a chemical reaction to couple the cell to each of the peptides in the cocktail, thereby forming said chemically coupled cell.

* * * * *

SEQUENCE LISTING

```
<160> NUMBER OF SEQ ID NOS: 26

<210> SEQ ID NO 1
<211> LENGTH: 20
<212> TYPE: PRT
<213> ORGANISM: Homo sapiens

<400> SEQUENCE: 1

Lys Tyr Leu Ala Thr Ala Ser Thr Met Asp His Ala Arg His Gly Phe
1               5                   10                  15

Leu Pro Arg His
            20

<210> SEQ ID NO 2
<211> LENGTH: 17
<212> TYPE: PRT
<213> ORGANISM: Homo sapiens

<400> SEQUENCE: 2

Glu Asn Pro Val Val His Phe Phe Lys Asn Ile Val Thr Pro Arg Thr
1               5                   10                  15

Pro

<210> SEQ ID NO 3
<211> LENGTH: 19
<212> TYPE: PRT
<213> ORGANISM: Homo sapiens

<400> SEQUENCE: 3

Leu Ser Arg Phe Ser Trp Gly Ala Glu Gly Gln Arg Pro Gly Phe Gly
1               5                   10                  15

Tyr Gly Gly

<210> SEQ ID NO 4
<211> LENGTH: 25
<212> TYPE: PRT
<213> ORGANISM: Homo sapiens

<400> SEQUENCE: 4
```

```
Ala Gln Gly Thr Leu Ser Lys Ile Phe Lys Leu Gly Gly Arg Asp Ser
1               5                   10                  15

Arg Ser Gly Ser Pro Met Ala Arg Arg
            20              25
```

<210> SEQ ID NO 5
<211> LENGTH: 16
<212> TYPE: PRT
<213> ORGANISM: Homo sapiens

<400> SEQUENCE: 5

```
His Cys Leu Gly Lys Trp Leu Gly His Pro Asp Lys Phe Val Gly Ile
1               5                   10                  15
```

<210> SEQ ID NO 6
<211> LENGTH: 20
<212> TYPE: PRT
<213> ORGANISM: Homo sapiens

<400> SEQUENCE: 6

```
Gly Gln Phe Arg Val Ile Gly Pro Arg His Pro Ile Arg Ala Leu Val
1               5                   10                  15

Gly Asp Glu Val
            20
```

<210> SEQ ID NO 7
<211> LENGTH: 21
<212> TYPE: PRT
<213> ORGANISM: Homo sapiens

<400> SEQUENCE: 7

```
Met Glu Val Gly Trp Tyr Arg Pro Pro Phe Ser Arg Val Val His Leu
1               5                   10                  15

Tyr Arg Asn Gly Lys
            20
```

<210> SEQ ID NO 8
<211> LENGTH: 17
<212> TYPE: PRT
<213> ORGANISM: Homo sapiens

<400> SEQUENCE: 8

```
Asp Glu Asn Pro Val Val His Phe Phe Lys Asn Ile Val Thr Pro Arg
1               5                   10                  15

Thr
```

<210> SEQ ID NO 9
<211> LENGTH: 18
<212> TYPE: PRT
<213> ORGANISM: Homo sapiens

<400> SEQUENCE: 9

```
Asp Glu Asn Pro Val Val His Phe Phe Lys Asn Ile Val Thr Pro Arg
1               5                   10                  15

Thr Pro
```

<210> SEQ ID NO 10
<211> LENGTH: 25
<212> TYPE: PRT
<213> ORGANISM: Homo sapiens

<400> SEQUENCE: 10

```
Asp Glu Asn Pro Val His Phe Phe Lys Asn Ile Val Thr Pro Arg
1               5                   10                  15

Thr Pro Pro Pro Ser Gln Gly Lys Gly
            20                  25
```

<210> SEQ ID NO 11
<211> LENGTH: 20
<212> TYPE: PRT
<213> ORGANISM: Homo sapiens

<400> SEQUENCE: 11

```
Val His Phe Phe Lys Asn Ile Val Thr Pro Arg Thr Pro Pro Pro Ser
1               5                   10                  15

Gln Gly Lys Gly
            20
```

<210> SEQ ID NO 12
<211> LENGTH: 25
<212> TYPE: PRT
<213> ORGANISM: Homo sapiens

<400> SEQUENCE: 12

```
Ala Ser Asp Tyr Lys Ser Ala His Lys Gly Leu Lys Gly Val Asp Ala
1               5                   10                  15

Gln Gly Thr Leu Ser Lys Ile Phe Lys
            20                  25
```

<210> SEQ ID NO 13
<211> LENGTH: 18
<212> TYPE: PRT
<213> ORGANISM: Homo sapiens

<400> SEQUENCE: 13

```
Gly Thr Glu Lys Leu Ile Glu Thr Tyr Phe Ser Lys Asn Tyr Gln Asp
1               5                   10                  15

Tyr Glu
```

<210> SEQ ID NO 14
<211> LENGTH: 18
<212> TYPE: PRT
<213> ORGANISM: Homo sapiens

<400> SEQUENCE: 14

```
Gly Phe Tyr Thr Thr Gly Ala Val Arg Gln Ile Phe Gly Asp Tyr Lys
1               5                   10                  15

Thr Thr
```

<210> SEQ ID NO 15
<211> LENGTH: 22
<212> TYPE: PRT
<213> ORGANISM: Homo sapiens

<400> SEQUENCE: 15

```
Ala Val Arg Gln Ile Phe Gly Asp Tyr Lys Thr Thr Ile Cys Gly Lys
1               5                   10                  15

Gly Leu Ser Ala Thr Val
            20
```

<210> SEQ ID NO 16
<211> LENGTH: 20
<212> TYPE: PRT
<213> ORGANISM: Homo sapiens

```
<400> SEQUENCE: 16

Asn Thr Trp Thr Thr Cys Gln Ser Ile Ala Phe Pro Ser Lys Thr Ser
1               5                   10                  15

Ala Ser Ile Gly
            20

<210> SEQ ID NO 17
<211> LENGTH: 20
<212> TYPE: PRT
<213> ORGANISM: Homo sapiens

<400> SEQUENCE: 17

Ser Lys Thr Ser Ala Ser Ile Gly Ser Leu Cys Ala Asp Ala Arg Met
1               5                   10                  15

Tyr Gly Val Leu
            20

<210> SEQ ID NO 18
<211> LENGTH: 20
<212> TYPE: PRT
<213> ORGANISM: Homo sapiens

<400> SEQUENCE: 18

Pro Ile Arg Ala Leu Val Gly Asp Glu Val Glu Leu Pro Cys Arg Ile
1               5                   10                  15

Ser Pro Gly Lys
            20

<210> SEQ ID NO 19
<211> LENGTH: 20
<212> TYPE: PRT
<213> ORGANISM: Homo sapiens

<400> SEQUENCE: 19

Glu Leu Pro Cys Arg Ile Ser Pro Gly Lys Asn Ala Thr Gly Met Glu
1               5                   10                  15

Val Gly Trp Tyr
            20

<210> SEQ ID NO 20
<211> LENGTH: 23
<212> TYPE: PRT
<213> ORGANISM: Homo sapiens

<400> SEQUENCE: 20

Glu Tyr Arg Gly Arg Thr Glu Leu Leu Lys Asp Ala Ile Gly Glu Gly
1               5                   10                  15

Lys Val Thr Leu Arg Ile Arg
            20

<210> SEQ ID NO 21
<211> LENGTH: 274
<212> TYPE: PRT
<213> ORGANISM: Homo sapiens

<400> SEQUENCE: 21

Met Gly Leu Leu Glu Cys Cys Ala Arg Cys Leu Val Gly Ala Pro Phe
1               5                   10                  15

Ala Ser Leu Val Ala Thr Gly Leu Cys Phe Phe Gly Val Ala Leu Phe
            20                  25                  30
```

```
            Cys Gly Cys Gly His Glu Ala Leu Thr Gly Thr Glu Lys Leu Ile Glu
                    35                  40                  45

Thr Tyr Phe Ser Lys Asn Tyr Gln Asp Tyr Glu Tyr Leu Ile Asn Val
             50                  55                  60

Ile His Ala Phe Gln Tyr Val Ile Tyr Gly Thr Ala Ser Phe Phe Phe
             65                  70                  75                  80

Leu Tyr Gly Ala Leu Leu Ala Glu Gly Phe Tyr Thr Thr Gly Ala
                                85                  90                  95

Val Arg Gln Ile Phe Gly Asp Tyr Lys Thr Thr Ile Cys Gly Lys Gly
                            100                 105                 110

Leu Ser Ala Thr Val Thr Gly Gly Gln Lys Gly Arg Gly Ser Arg Gly
                        115                 120                 125

Gln His Gln Ala His Ser Leu Glu Arg Val Cys His Cys Leu Gly Lys
                    130                 135                 140

Trp Leu Gly His Pro Asp Lys Ile Thr Tyr Ala Leu Thr Val Val Trp
            145                 150                 155                 160

Leu Leu Val Phe Ala Cys Ser Ala Val Pro Val Tyr Ile Tyr Phe Asn
                            165                 170                 175

Thr Trp Thr Thr Cys Gln Ser Ile Ala Phe Pro Ser Lys Thr Ser Ala
                        180                 185                 190

Ser Ile Gly Ser Leu Cys Ala Asp Ala Arg Met Tyr Gly Val Leu Pro
                    195                 200                 205

Trp Asn Ala Phe Pro Gly Lys Val Cys Gly Ser Asn Leu Leu Ser Ile
                            210                 215                 220

Cys Lys Thr Ala Glu Phe Gln Met Thr Phe His Leu Phe Ile Ala Ala
            225                 230                 235                 240

Phe Val Gly Ala Ala Ala Thr Leu Val Ser Leu Leu Thr Phe Met Ile
                            245                 250                 255

Ala Ala Thr Tyr Asn Phe Ala Val Leu Lys Leu Met Gly Arg Gly Thr
                        260                 265                 270

Lys Phe

<210> SEQ ID NO 22
            <211> LENGTH: 170
            <212> TYPE: PRT
            <213> ORGANISM: Homo sapiens

<400> SEQUENCE: 22

Ala Ser Gln Lys Arg Pro Ser Gln Arg His Gly Ser Lys Tyr Leu Ala
            1               5                   10                  15

Thr Ala Ser Thr Met Asp His Ala Arg His Gly Phe Leu Pro Arg His
                            20                  25                  30

Arg Asp Thr Gly Ile Leu Asp Ser Leu Gly Arg Phe Phe Gly Gly Asp
                        35                  40                  45

Arg Gly Ala Pro Lys Arg Gly Ser Gly Lys Asp Ser His His Ala Ala
                    50                  55                  60

Arg Thr Thr His Tyr Gly Ser Leu Pro Gln Lys Ser His Gly Arg Thr
            65                  70                  75                  80

Gln Asp Glu Asn Pro Val Val His Phe Phe Lys Asn Ile Val Thr Pro
                            85                  90                  95

Arg Thr Pro Pro Pro Ser Gln Gly Lys Gly Arg Gly Leu Ser Leu Ser
                        100                 105                 110

Arg Phe Ser Trp Gly Ala Glu Gly Gln Arg Pro Gly Phe Gly Tyr Gly
                    115                 120                 125
```

```
Gly Arg Ala Ser Asp Tyr Lys Ser Ala His Lys Gly Leu Lys Gly Val
            130                 135                 140

Asp Ala Gln Gly Thr Leu Ser Lys Ile Phe Lys Leu Gly Gly Arg Asp
145                 150                 155                 160

Ser Arg Ser Gly Ser Pro Met Ala Arg
                165                 170

<210> SEQ ID NO 23
<211> LENGTH: 247
<212> TYPE: PRT
<213> ORGANISM: Homo sapiens

<400> SEQUENCE: 23

Met Ala Ser Leu Ser Arg Pro Ser Leu Pro Ser Cys Leu Cys Ser Phe
1               5                   10                  15

Leu Leu Leu Leu Leu Gln Val Ser Ser Tyr Ala Gly Gln Phe
            20                  25                  30

Arg Val Ile Gly Pro Arg His Pro Ile Arg Ala Leu Val Gly Asp Glu
            35                  40                  45

Val Glu Leu Pro Cys Arg Ile Ser Pro Gly Lys Asn Ala Thr Gly Met
50                  55                  60

Glu Val Gly Trp Tyr Arg Pro Pro Phe Ser Arg Val Val His Leu Tyr
65                  70                  75                  80

Arg Asn Gly Lys Asp Gln Asp Gly Asp Gln Ala Pro Glu Tyr Arg Gly
            85                  90                  95

Arg Thr Glu Leu Leu Lys Asp Ala Ile Gly Glu Gly Lys Val Thr Leu
            100                 105                 110

Arg Ile Arg Asn Val Arg Phe Ser Asp Glu Gly Gly Phe Thr Cys Phe
            115                 120                 125

Phe Arg Asp His Ser Tyr Gln Glu Glu Ala Ala Met Glu Leu Lys Val
            130                 135                 140

Glu Asp Pro Phe Tyr Trp Val Ser Pro Gly Val Leu Val Leu Leu Ala
145                 150                 155                 160

Val Leu Pro Val Leu Leu Leu Gln Ile Thr Val Gly Leu Val Phe Leu
            165                 170                 175

Cys Leu Gln Tyr Arg Leu Arg Gly Lys Leu Arg Ala Glu Ile Glu Asn
            180                 185                 190

Leu His Arg Thr Phe Asp Pro His Phe Leu Arg Val Pro Cys Trp Lys
            195                 200                 205

Ile Thr Leu Phe Val Ile Val Pro Val Leu Gly Pro Leu Val Ala Leu
210                 215                 220

Ile Ile Cys Tyr Asn Trp Leu His Arg Arg Leu Ala Gly Gln Phe Leu
225                 230                 235                 240

Glu Glu Leu Arg Asn Pro Phe
            245

<210> SEQ ID NO 24
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Cit
<220> FEATURE:
<221> NAME/KEY: MOD_RES
```

```
<222> LOCATION: (14)..(14)
<223> OTHER INFORMATION: Cit

<400> SEQUENCE: 24

Ala Ser Thr Met Asp His Ala Xaa His Gly Phe Leu Pro Xaa His Arg
1               5                   10                  15

Asp Thr Gly Ile Leu
            20

<210> SEQ ID NO 25
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Cit
<220> FEATURE:
<221> NAME/KEY: MOD_RES
<222> LOCATION: (16)..(16)
<223> OTHER INFORMATION: Cit

<400> SEQUENCE: 25

Ser Trp Gly Ala Glu Gly Gln Xaa Pro Gly Phe Gly Tyr Gly Gly Xaa
1               5                   10                  15

Ala

<210> SEQ ID NO 26
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Cit

<400> SEQUENCE: 26

Ser Lys Ile Phe Lys Leu Gly Gly Xaa Asp Ser Arg Ser Gly Ser Pro
1               5                   10                  15

Met Ala Arg Arg
            20
```